United States Patent
Nagao et al.

(10) Patent No.: US 10,570,034 B2
(45) Date of Patent: Feb. 25, 2020

(54) FLOCCULATION MONITORING APPARATUS, FLOCCULATION MONITORING METHOD, AND FLOCCULATION SYSTEM

(71) Applicant: KURITA WATER INDUSTRIES LTD., Tokyo (JP)

(72) Inventors: Nobuaki Nagao, Tokyo (JP); Yasuhiro Mugibayashi, Tokyo (JP)

(73) Assignee: KURITA WATER INDUSTRIES LTD., Tokyo (JP)

( * ) Notice: Subject to any disclaimer, the term of this patent is extended or adjusted under 35 U.S.C. 154(b) by 6 days.

(21) Appl. No.: 15/743,430

(22) PCT Filed: Jul. 21, 2016

(86) PCT No.: PCT/JP2016/003406
§ 371 (c)(1),
(2) Date: Jan. 10, 2018

(87) PCT Pub. No.: WO2017/013879
PCT Pub. Date: Jan. 26, 2017

(65) Prior Publication Data
US 2018/0201527 A1    Jul. 19, 2018

(30) Foreign Application Priority Data

Jul. 22, 2015   (JP) .................. 2015-144609

(51) Int. Cl.
*C02F 1/52* (2006.01)
*B01D 21/30* (2006.01)
(Continued)

(52) U.S. Cl.
CPC ................ *C02F 1/52* (2013.01); *B01D 21/30* (2013.01); *G01N 15/06* (2013.01); *G01N 21/49* (2013.01)

(58) Field of Classification Search
CPC ........... B01D 21/30; C02F 1/52; G01N 15/06; G01N 21/49; G01N 21/51; G01N 2015/0693
See application file for complete search history.

(56) References Cited

U.S. PATENT DOCUMENTS

2010/0035235 A1   2/2010  Gabriel
2011/0013185 A1   1/2011  Obata
(Continued)

FOREIGN PATENT DOCUMENTS

CN    102203587 A    9/2011
CN    102422179 A    4/2012
(Continued)

OTHER PUBLICATIONS

International Preliminary Report on Patentability (Form PCT/IB/338) issued in counterpart International Application No. PCT/JP2016/003406 dated Jan. 23, 2018, with Form PCT/IB/373, PCT/ISA/237, and PCT/IB326, with English translation (11 pages).
(Continued)

*Primary Examiner* — Kara E. Geisel
(74) *Attorney, Agent, or Firm* — Westerman, Hattori, Daniels & Adrian, LLP

(57) ABSTRACT

A flocculation monitoring apparatus and a flocculation monitoring method are provided, and the flocculation monitoring apparatus and the flocculation monitoring method are capable of stably measuring a flocculation state of water to be treated even when the number (density) of flocs has increased. A measurement-light applying part (laser-light applying part 10) applies a measurement light to a measurement region (18) in the water to be treated (8) and a scattered-light receiving part (12) receives a scattered light due to particles of the water to be treated. A measurement value arithmetic part (arithmetic circuit 48) calculates an index related to flocculation of the water to be treated, by (Continued)

using an amplitude of a light reception signal acquired in the scattered-light receiving part.

10 Claims, 15 Drawing Sheets

(51) Int. Cl.
*G01N 15/06* (2006.01)
*G01N 21/49* (2006.01)

(56) References Cited

U.S. PATENT DOCUMENTS

| | | |
|---|---|---|
| 2016/0047730 A1 | 2/2016 | Tanaka |
| 2016/0161393 A1 | 6/2016 | Tahara |
| 2017/0144161 A1* | 5/2017 | Hindson ............... B01F 3/0807 |

FOREIGN PATENT DOCUMENTS

| | | |
|---|---|---|
| EP | 0108605 A2 | 5/1984 |
| JP | 7-171307 A | 7/1995 |
| JP | 2002-195947 A | 7/2002 |
| JP | 2005-241338 A | 9/2005 |
| JP | 2005-249538 A | 9/2005 |
| JP | 2007-57516 A | 3/2007 |
| JP | 2007-231487 A | 9/2007 |
| JP | 2007-263856 A | 10/2007 |
| JP | 2007-271333 A | 10/2007 |
| TW | 201447262 A | 12/2014 |
| WO | 2009/116633 A1 | 9/2009 |
| WO | 2010/017001 A2 | 2/2010 |
| WO | 2010/124038 A2 | 10/2010 |
| WO | 2010/141040 A1 | 12/2010 |
| WO | 2015/012004 A1 | 1/2015 |

OTHER PUBLICATIONS

Office Action dated Aug. 30, 2018, issued in counterpart Chinese Application No. 201680042242.4, with partial English translation. (16 pages).

Notification of Reasons for Refusal dated Jun. 20, 2017, issued in counterpart Japanese Patent Application No. 2015-144609, w/English translation (7 pages).

Notification of Reasons for Refusal dated Oct. 17, 2017, issued in counterpart Japanese Patent Application No. 2015-144609, w/English translation (7 pages).

International Search Report dated Oct. 4, 2016, issued in counterpart International Application No. PCT/JP2016/003406, w/English translation (3 pages).

Written Opinion dated Oct. 4, 2016, issued in counterpart International Application No. PCT/JP2016/003406 in Japanese (3 pages).

Office Action dated Apr. 8, 2019, issued in counterpart CN Application No. 201680042242.4, with partial English translation (15 pages).

Cheng, W. P., et al., "A novel method for on-line evaluation of floc size in coagulation process", Water Research, 2008, vol. 42, No. 10, pp. 2691-2697; cited in EESR dated Feb. 19, 2019.

Extended (supplementary) European Search Report dated Feb. 19, 2019, issued in counterpart EP Application No. 16827445.4. (8 pages).

Office Action dated Oct. 24, 2019, issued in counterpart CN application No. 201680042242.4, with English translation. (17 pages).

Office Action dated Dec. 20, 2019 issued in counterpart EP application No. 16827445.4. (5 pages).

Office Action dated Nov. 27, 2019 issued in counterpart TW application No. 105122972 with English translation. (15 pages).

* cited by examiner

FLOCCULATION MONITORING APPARATUS, FLOCCULATION MONITORING METHOD, AND FLOCCULATION SYSTEM

TECHNICAL FIELD

The present invention relates to a monitoring technique of flocculation treatment of water to be treated such as purified water, industrial water, and wastewater, for example, and a technique of using the same.

BACKGROUND ART

In flocculation treatment of water to be treated such as purified water, industrial water, and wastewater, for example, SS (suspended solids) in water to be treated is subjected to the flocculation treatment with an inorganic flocculant or an organic flocculant before solid-liquid separation such as sedimentation separation, pressure floatation separation, centrifugal separation, sand filtration, membrane separation. The flocculation state of the SS varies depending on pH, a flocculant dosing amount, stirring conditions, etc., and if the flocculation treatment is not performed under appropriate conditions, water quality deterioration may be caused in the water to be treated, and may affect the solid-liquid separation treatment at the next step.

For such flocculation treatment, a method of setting flocculation conditions in a laboratory test exists; however, if it takes time to set the flocculation conditions in actual flocculation treatment, the water quality of the water to be treated varies and the flocculation state of the SS cannot accurately be comprehended in some cases. Therefore, to set optimum flocculation conditions such as pH, a flocculant dosing amount, and stirring conditions, it is important to monitor a treatment state of the water to be treated during the flocculation treatment in real time and to monitor the flocculation state of the SS.

With respect to this flocculation monitoring, it is known that a laser light is applied to water to be treated to receive a scattered light from particles in the water to be treated and that after AM (amplitude modulation) detection is applied to the light reception signal, a minimum value of signal intensity is obtained so as to obtain a flocculant dosing amount from this minimum value (e.g., Patent Literature 1). In this flocculation monitoring, the minimum value of signal intensity of the scattered light is obtained to distinguish and detect a scattered light due to non-flocculated suspended solids from the scattered light due to flocculated matter in the water to be treated.

It is known that the laser light used for this flocculation monitoring is implemented by using a laser light emitted at predetermined time intervals by intermittently driving a laser diode (e.g., Patent Literature 2). An operating time of a laser-emitting element is extended by a light-emitting form shortening this light-emitting time.

CITATION LIST

Patent Literature

Patent Literature 1: Japanese Laid-Open Patent Publication No. 2002-195947

Patent Literature 2: Japanese Laid-Open Patent Publication No. 2005-241338

SUMMARY OF INVENTION

Technical Problem

In flocculation treatment of water to be treated, a dosing system is used that measures a concentration of SS not taken into generated flocs and that controls a flocculant dosing amount based on this measurement value. For the SS concentration measurement, a laser light is applied to a measurement region of the water to be treated to receive a scattered light from the measurement region, and a measurement value indicative of the SS concentration is obtained from a signal level acquired through photoelectric conversion of the scattered light.

In this dosing system, an upper limit value of a dosing amount is specified and the dosing system retains a minimum value of the signal level described above in a certain period to evaluate a flocculation state. Since upper limit values are specified for the SS amount and the dosing amount in this method, stable measurement can be performed when an amount of formed flocs is suppressed.

However, depending on water to be treated, a concentration of SS components in the water to be treated may be high, or the water to be treated may be treated only with an inorganic flocculant. Since these cases lead to a high floc density and small flocs, gaps between the flocs become smaller. The frequency that the light applied to the water to be treated strikes the flocs for the flocs to occur the scattered light becomes higher, and the light is shielded by the flocs in front of a light receiving part, so that the scattered light itself attenuates before arriving at the light receiving part. This causes a problem that water to be treated having a high concentration and small flocs makes accurate measurement difficult.

When a general PID (proportional integral derivative) control is assumed, the measurement value used for the dosing control must be a measurement value correlated with SS remaining between flocs, in the dosing control based on the minimum value of the signal level in a certain period as described above. Therefore, when opportunities for turbidity measurement using the SS between the flocs decrease due to an increase in the number (density) of flocs, a sufficient measurement time required for measurement of the minimum value must be ensured to obtain the minimum value correlated with the SS so as to update the minimum value; however, a longer time interval of updating the minimum value causes a problem that a capability of compensating a control delay is lost in the dosing system.

Patent Literatures 1 and 2 do not disclose or suggest such requirements and problems and do not disclose or suggest a configuration etc. for solving the problems.

In view of the problems, an object of the present invention is to provide a flocculation monitoring apparatus or a flocculation monitoring method capable of stably measuring a flocculation state of water to be treated even when the number (density) of flocs has increased.

Another object of the present invention is to implement a flocculation system using the flocculation monitoring apparatus or the flocculation monitoring method to provide a reliable flocculation treatment without impairing a compensation capability necessary for dosing control even if the number (density) of flocs increases.

Solution to Problem

To achieved the objects, an aspect of a flocculation monitoring apparatus of the present invention provides a flocculation monitoring apparatus monitoring a treatment, state of water to be treated that is subjected to a flocculation treatment, and the apparatus includes a measurement-light applying part applying a measurement light to a measurement region in the water to be treated; a scattered-light receiving part receiving a scattered light due to particles of the water to be treated in the measurement region; and a measurement value arithmetic part calculating an index related to flocculation of the water to be treated, by using an amplitude of a light reception signal acquired in the scattered-light receiving part.

In the flocculation monitoring apparatus, the measurement value arithmetic part may include an amplitude measuring means measuring the amplitude of the light reception signal acquired in the scattered-light receiving part.

In the flocculation monitoring apparatus, the measurement value arithmetic part may further include a minimum value measuring means measuring from the light reception signal a minimum value of the signal and calculate the index related to the flocculation by using a measurement result of the amplitude measuring means or measurement results of the amplitude measuring means and the minimum value measuring means.

In the flocculation monitoring apparatus, the measurement value arithmetic part may calculate an occurrence rate or occurrence frequency of a specific amplitude based on a measurement result of the amplitude to calculate the index related to the flocculation, and the specific amplitude may have an occurrence frequency increasing as flocculation progresses.

To achieved the objects, an aspect of a flocculation monitoring method of the present invention provides a flocculation monitoring method of monitoring a treatment state of water to be treated that is subjected to a flocculation treatment, and the method includes a measurement-light applying step of applying a measurement light to a measurement region in the water to be treated; a scattered-light receiving step of receiving a scattered light due to particles of the water to be treated in the measurement region; a signal processing step of extracting a measurement value indicative of intensity of the scattered light from a light reception signal acquired at the scattered-light receiving step; and a measurement value arithmetic step of measuring an amplitude of the scattered light from the measurement value indicative of intensity of the scattered light and calculating an index related to flocculation by using a measurement result of the amplitude.

To achieved the objects, an aspect of a flocculation system of the present invention provides a flocculation system performing a flocculation treatment for water to be treated; the system includes a treated water tank storing the water to be treated, a flocculation monitoring means monitoring a treatment state of the water to be treated in the treated water tank, and a dosing means injecting into the water to be treated a flocculant of a dosing amount corresponding to the treatment state; the monitoring means is a flocculation monitoring apparatus monitoring the treatment state of the water to be treated that is subjected to a flocculation treatment, and includes a measurement-light applying part applying a measurement light to a measurement region of the water to be treated, a scattered-light receiving part receiving a scattered light due to particles of the water to be treated in the measurement region, and a measurement value arithmetic part calculating an index related to flocculation of the water to be treated, by using an amplitude of a light reception signal acquired in the scattered-light receiving part; and the dosing means adjusts an injection amount of the flocculant based on the index related to the flocculation.

Advantageous Effects of Invention

According to the present invention, any of the following effect, can be acquired.

<Flocculation Monitoring Apparatus or Flocculation Monitoring Method>

(1) Even if a large amount of flocs is generated in the water to be treated during flocculation and the floc density becomes higher, the treatment state of the water to be treated can stably be measured.

(2) The treatment state of the water to be treated during flocculation can accurately be comprehended in real time. Consequently, a flocculant dosing amount can be selected depending on the treatment state.

<Flocculation System>

(1) The treatment state of the water to be treated can stably be measured to comprehend the treatment state of the water to be treated during the flocculation treatment in real time and, based on this state, the flocculation conditions of the water to be treated and the flocculant dosing amount can be obtained.

(2) The dosing amount can be optimized for the water to be treated and the stable flocculation treatment can be performed so as to improve flocculation efficiency.

Other objects, features, and advantages of the present invention will become more apparent by reference to the accompanying drawings and embodiments.

DESCRIPTION OF EMBODIMENTS

[First Embodiment]

Figure 1:
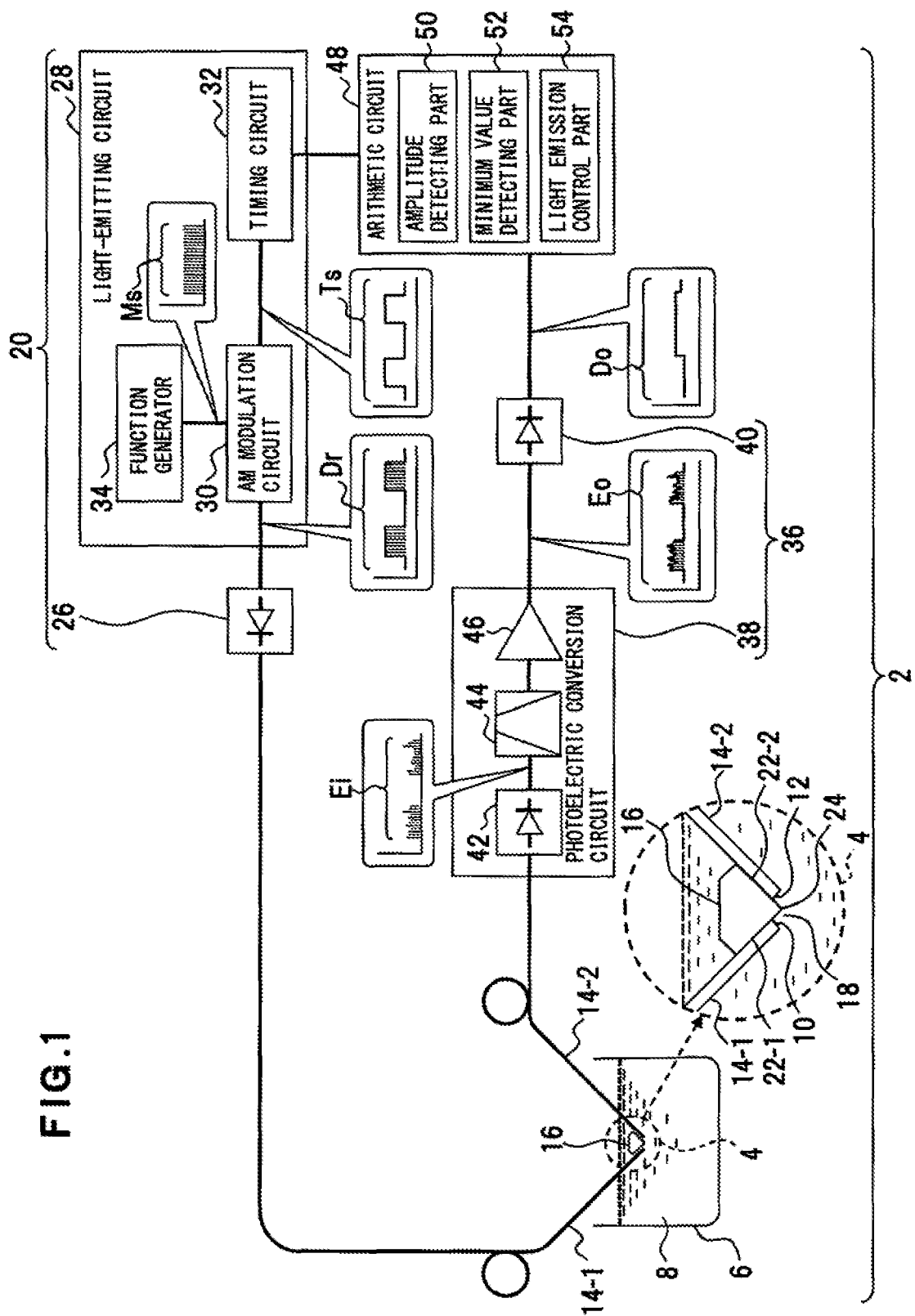
FIG. 1 is a block diagram of an example of a flocculation monitoring apparatus according to a first embodiment.

FIG. 1 shows a flocculation monitoring apparatus according to a first embodiment. The configuration shown in FIG. 1 is an example, and a flocculation monitoring apparatus, a flocculation monitoring method, or a flocculation system of the present invention is not limited to this configuration.

This flocculation monitoring apparatus 2 includes a sensor part 4. For instance, the sensor part 4 is maintained in a submerged state in water to be treated 8 stored in a flocculation tank 6. The flocculation tank 6 is an example of a treated water tank for storing the water to be treated 8 and additionally has a function of performing a flocculation treatment of the water to be treated 8.

The sensor part 4 includes a laser-light applying part 10 and a scattered-light receiving part 12. The laser-light applying part 10 is an example of a measurement-light applying part applying a measurement light used for monitoring flocculation and is formed by a light exit end portion of a first optical fiber 14-1 guiding a laser light that is an example of the measurement light. The scattered-light receiving part 12 is formed by a light entry end portion of a second optical fiber 14-2 guiding a scattered light.

A measurement region 18 is set between the laser-light applying part 10 and the scattered-light receiving part 12 with a shielding member 16 interposed therebetween. To this measurement region 18, the laser light emitted by a laser-light emitting part 20 is applied from the laser-light applying part 10. This measurement region 18 is an example of an application region of the laser light in the water to be treated 8. When the laser light is applied to the measuring region 18, the laser light is scattered by particles in the water to be treated 8, and a scattered light is generated. Therefore, the scattered-light receiving part 12 receives this scattered light from the measurement region 18. In this case, if flocs are present in the measurement area 18, the flocs affect the scattered light.

shielding member 16 is a means for fixing and supporting the optical fibers 14-1, 14-2 as well as a means for shielding natural light to the measurement region 18. This shielding member 16 includes, for example, a vertex portion 24 in which a first supporting part 22-1 fixing and supporting the optical fiber 14-1 and a second supporting part 22-2 supporting the optical fiber 14-2 have a certain angle. The angle of the vertex portion 24 is preferably 90 degrees, for example, or may be other angles. The vertex portion 24 faces the measurement region 18 and is interposed between the laser-light applying part 10 and the scattered-light receiving part 12. Therefore, the laser light from the laser-light applying part 10 can be prevented from entering the scattered-light receiving part 12, and the scattered-light receiving part 12 can receive a scattered light on the particle side in the measurement region 18.

The laser-light emitting part 20 includes a laser-emitting element 26 and a light-emitting circuit 28. The laser-emitting element 26 is an example of a laser light source emitting a laser light. The laser light source is preferably a laser diode, or may be any element or device capable of producing a laser light. The measurement light used for monitoring flocculation is not limited to laser light. Any light that strikes the particles and causes a scattered light may be used for monitoring flocculation, by using a measurement light excellent in directionality such as laser light, the light can efficiently be applied to the measurement region 18. When such a measurement light is used, a light-emitting part that includes a light-emitting element emitting a measurement light and a light-emitting circuit driving the light-emitting element may be used. For the measurement light, for example, a light-emitting diode may be used.

The light-emitting circuit 28 is an example of a drive means of the laser-emitting element 26. For example, the light-emitting circuit 28 includes an AM (amplitude modulation) modulation circuit 30, a timing circuit 32, and a function generator 34. The AM modulation circuit 30 performs amplitude modulation (AM modulation) at a timing signal Ts with a modulation signal Ms having a predetermined frequency f to output a light emission signal Dr having an amplitude of the predetermined frequency f and intermitting at predetermined time intervals. Receiving this emission signal Dr, the laser-emitting element 26 changes with the modulation signal Ms and alternates between emission and non-emission at predetermined time intervals according to the timing signal Ts. This leads to shortening of the light-emitting time of the laser-emitting element 26 for flocculation monitoring. Even if a light-emitting element such as a laser diode having a short emission lifetime of several thousand hours is used for the laser-emitting element 26, deterioration due to continuous lighting can be prevented, so that the operating time can be extended.

The timing circuit 32 generates the timing signal Ts. For example, the timing signal Ts is a pulse signal intermitting in a constant period. This timing signal Ts is used as synchronization information of an arithmetic process for a flocculation index related to flocculation of the water to be treated 8. Therefore, the timing signal Ts synchronizes the light emission of the laser-emitting element 26 with the arithmetic process for the flocculation index.

The function generator 34 is an example of an oscillator oscillating the modulation signal Ms. This modulation signal Ms preferably has the frequency f at which the influence of natural light, on the laser light can be avoided and, for example, f that is 70 to 150 [kHz] is used. The signal form is a periodic signal having the same amplitude and the waveform is any of a sine wave, a triangular wave, a rectangular wave, etc.

When the laser light acquired by the laser-light emitting part 20 as described above is applied to the measurement region 18, a scattered light scattered by fine colloidal particles present in the measurement region 18 is incident on the scattered-light receiving part 12. In this case, the fine colloidal particles are non-flocculated colloidal particles. The scattered light acquired by the fine colloidal particles has the same frequency as the laser light applied from the laser-light applying part 10 and has a form of intermitting in a constant period. A reflected light reflected by flocs present in the measurement region 18 is also incident on the scattered-light receiving part 12.

The light reception output of the scattered-light receiving part 12 is guided through the optical fiber 14-2 to a signal processing part 36. The signal processing part 36 performs photoelectric conversion and removal of noise components, and extracts a level signal indicative of the intensity of the scattered light and a measurement values indicative of the intensity of the scattered light from this level signal. The signal processing part 36 includes, for example, a photoelectric conversion circuit 38 and a detection circuit 40.

The photoelectric conversion circuit 38 includes a photodetector 42, a bandpass filter 44, and an amplifier 46. The photodetector 42 receives the scattered light guided through the optical fiber 14-2 and converts the scattered light into an electric signal Ei. The bandpass filter 44 cuts off a noise component from the electric signal Ei and extracts a signal component of the modulation signal Ms. By setting the cutoff frequency of the bandpass filter 44, an unnecessary variation component is removed so as to output the signal component of the modulation signal Ms. The amplifier 46 amplifies the signal component of the modulation signal Ms in the scattered light and outputs a light reception signal Eo having an amplitude level corresponding to the scattered light. In the photoelectric conversion circuit 38, a photodiode may be used instead of the photodetector 42, and a high-pass filter may be used instead of the bandpass filter 44. By using these filters, a direct-current noise component generated by reception of non-measurement light such as natural light and illumination light can be cut off.

The detection circuit 40 detects an output signal Do by AM detection (envelope detection) from the light reception signal Eo. This output signal Do is an example of a light reception signal and indicates a level of a direct-current component of the light reception signal Eo. This level indicates a scattered light level due to the particles in the water to be treated containing the fine colloidal particles. In other words, the level includes a noise component that is a scattered light of other than the fine colloidal particles and a reflection component due to flocs.

The output of this detection circuit 40 is applied to an arithmetic circuit 48. The arithmetic circuit 48 is an example of a measurement value arithmetic part and includes an amplitude detecting part 50 and a minimum value detecting part 52. The arithmetic circuit 48 records the level (signal intensity) of the output signal Do input to the arithmetic circuit 48 in a data recording part 64 of a memory part 60 (FIG. 2) and measures the output signal Do by the amplitude detecting part 50 and the minimum value detecting part 52. The arithmetic circuit 48 determines a flocculation level of the water to be treated, by using these measurement results, and outputs a flocculation index indicative of this flocculation level. The flocculation level indicated by the flocculation index is represented by, for example, a "low level", an "appropriate level", an "appropriate or excessive level", or an "excessive level". The arithmetic circuit 48 further includes a light emission control part 54 and outputs to the timing circuit 32 a control signal (the timing signal Ts) synchronized with the light emission of the laser-emitting element 26 and the arithmetic process for the flocculation index.

The amplitude detecting part 50 is an example of an amplitude detecting means and an amplitude measuring means, and has functions of both amplitude detection and amplitude measurement. The amplitude detecting part 50 detects inflection points of the level of the output signal Do recorded in the data recording part 64 and measures a peak value of each of the inflection points. Through the detection of the inflection points, the amplitude detecting part 50 detects the occurrence of amplitude of the output signal Do. In particular, the amplitude detecting part 50 detects first inflection points at which the output signal Do changes from rising to falling and second inflection points at which the signal changes from falling to rising, and detects the adjacent first and second inflection points to detect the occurrence of amplitude. The amplitude detecting part 50 obtains a level difference between the adjacent first and second inflection points through the measurement of the peak value so as to measure the magnitude of amplitude of the output signal Do. With these functions, the amplitude detecting part 50 can measure the number of occurrences of the amplitude of the output signal Do for each level of the amplitude (i.e., amplitude range).

The minimum value detecting part 52 is an example of a minimum value measuring means comparing the levels of the output signal Do recorded in the data recording part 64 to calculate the minimum measurement value of the output signal Do.

Figure 2:
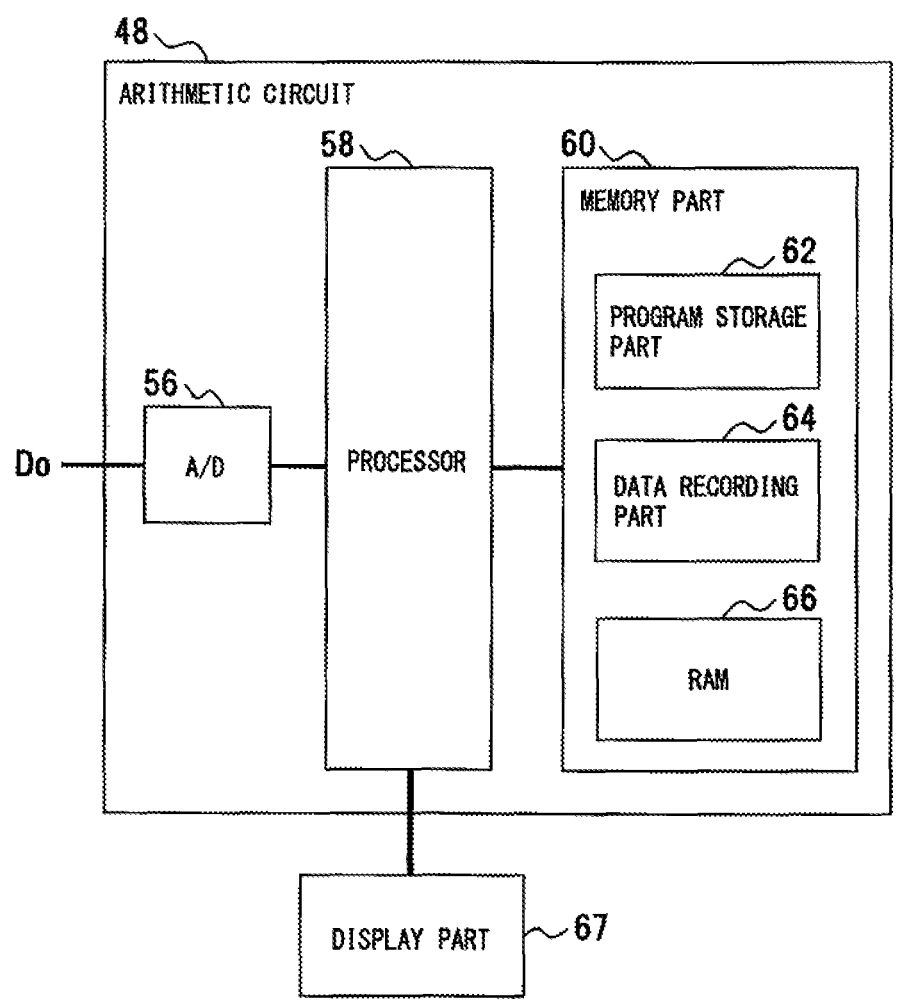
FIG. 2 is a block diagram of an example of an arithmetic circuit.

For example, as shown in FIG. 2, the arithmetic circuit 48 is realized by a circuit including a computer such as a microprocessor. The arithmetic circuit 48 includes an analog-digital converter (A/D) 56, a processor 58, and the memory part 60. The A/D 56 converts the output signal Do to a digital signal. The output signal of the A/D 56 indicates the level of the output signal Do as a digital value, and is used for digital processing of the amplitude detecting part 50 and the minimum value detecting part 52.

The processor 58 executes an OS (operating system) and a flocculation program in a program storage part 62 of the memory part 60 to function as the amplitude detecting part 50, the minimum value detecting part 52, and the light emission control part 54 described above.

The memory part 60 is an example of a recording part and includes the program storage part 62, the data recording part 64, and a RAM (random-access memory) 66. In the program storage part 62, the OS, the flocculation program described above, etc. are stored as programs. In the data recording part 64, the level of the output signal Do is recorded. The RAM 66 is used as a work area for information processing.

The arithmetic results of the processor 58 is output to a display part 67. For example, a liquid crystal display (LCD) is used for this display part 67. This display part 67 displays measurement values used for arithmetic operations of the processor 58 and various data including arithmetic results such as a minimum measurement value and an occurrence frequency of the amplitude of the output signal Do.

<Measurement Principle of Flocculation State According to Amplitude Detection>

As a result of analysis of monitoring data of flocculation of water to be treated, it was found that the occurrence frequency of the first and second inflection points of the output signal Do, i.e., the amplitude of the output signal Do, has a certain relationship with a flocculation state for each amplitude range. Focusing on this certain relationship, the amplitude detecting part 50 measures a flocculation state by using the inflection points. The certain relationship described above will be described later.

(1) First Measurement Principle

In a first measurement principle, it is assumed that measurement is performed in the water to be treated 8 in which flocs having a particle diameter smaller than the diameter of the measurement region IS enter and exit the measurement region 18.

[Generated Scattered Light Intensity]

Figure 3:
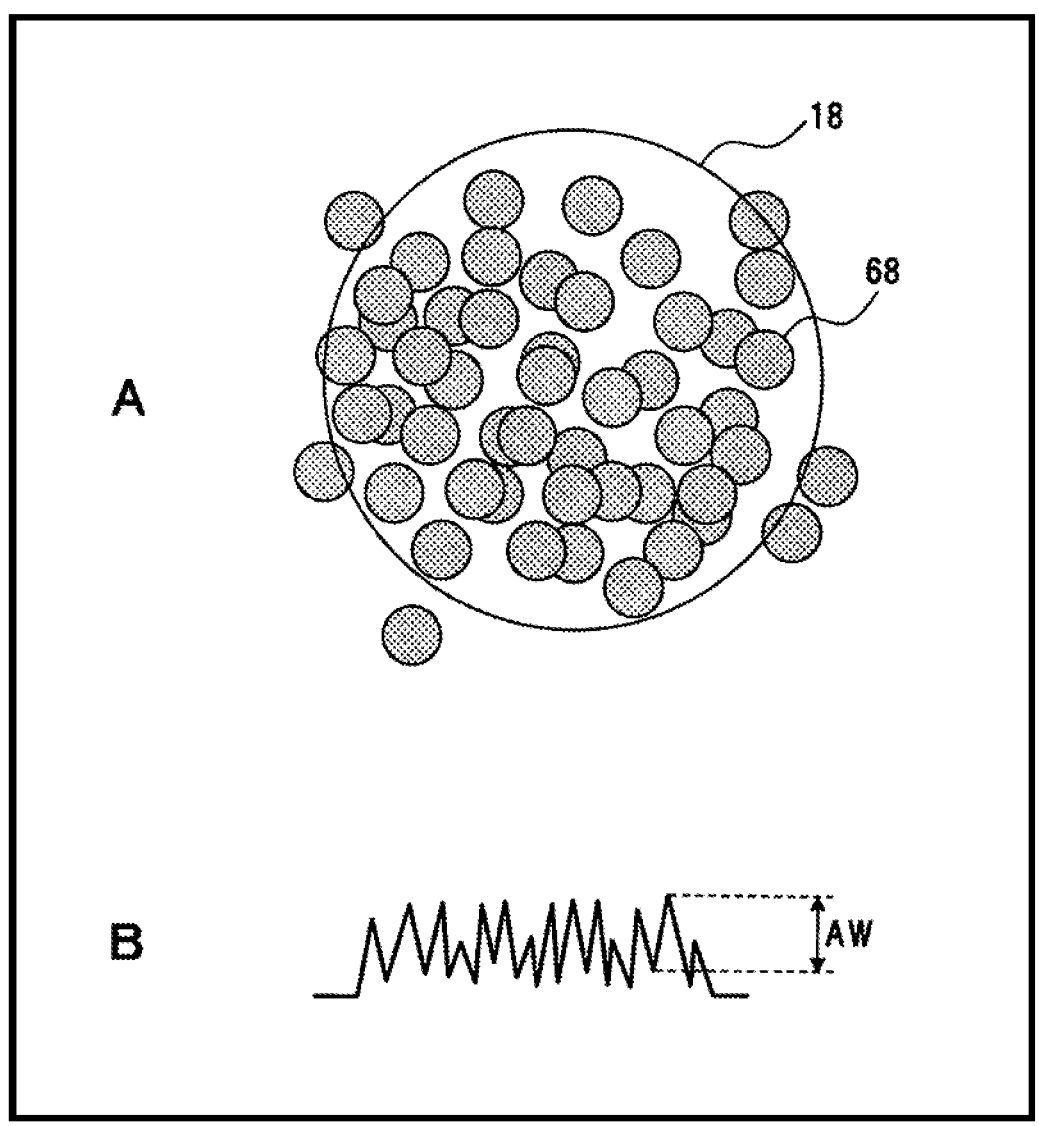
FIG. 3 is a diagram of examples of a floc generation state and a detection waveform of an output signal.
Figure 4:
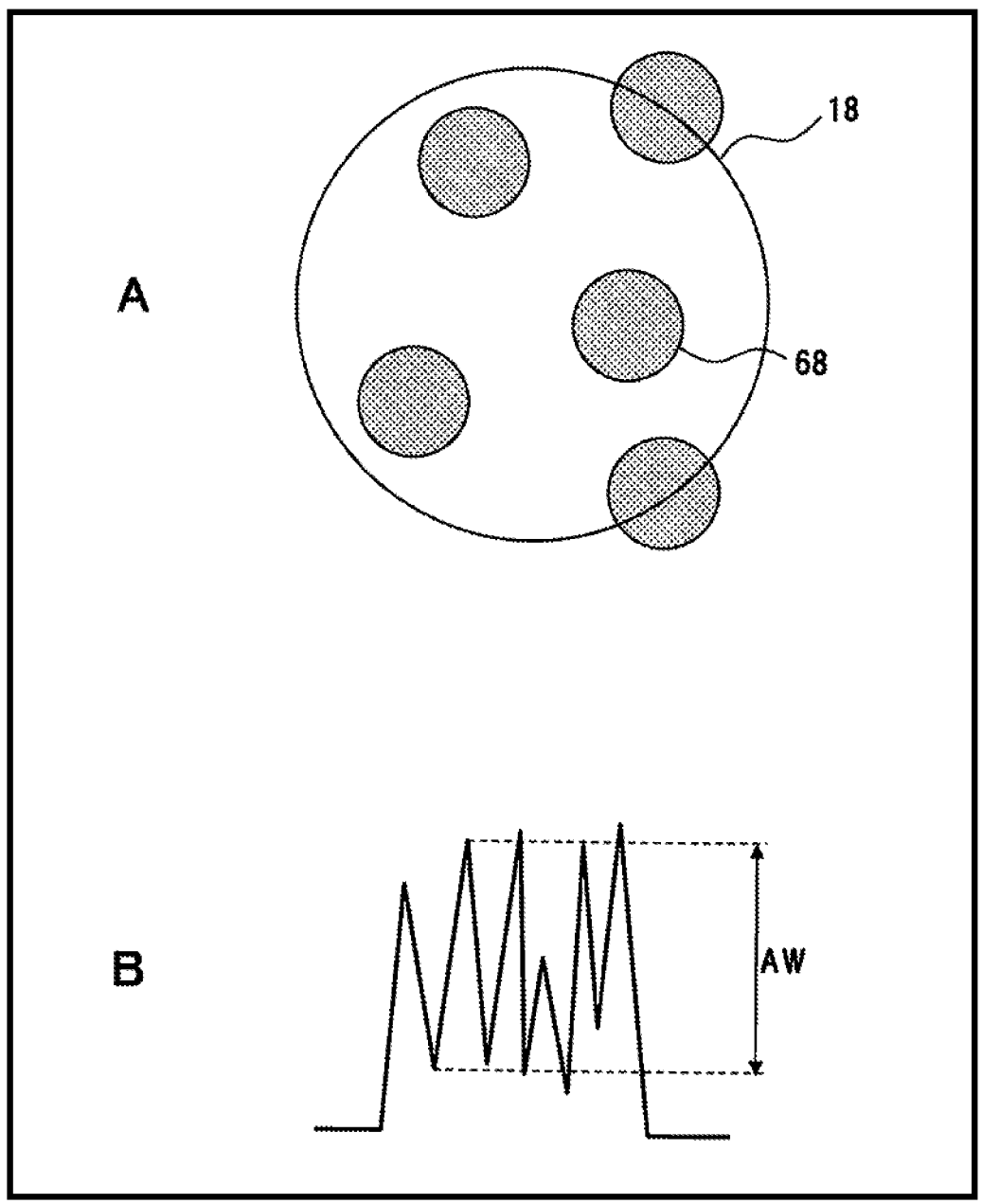
FIG. 4 is a diagram of examples of a floc generation state and a detection waveform of an output signal.

A of FIG. 3 and A of FIG. 4 show examples of floc generation states. A of FIG. 3 shows an example when the particle diameter is small and A of FIG. 4 shows an example when the particle diameter is large. In the generation state shown in A of FIG. 3, flocs 68 are generated at a high density or number density in the water to be treated 8. The measurement region 18 is set to a circular region having a diameter of about 1 [mm]. The flocs 68 having a particle diameter of 1 [mm] or less are generated, to this measurement region 18. In the generation state shown in A of FIG. 4, similar to the generation state shown in A of FIG. 3, the flocs 68 are generated at a high density or number density in the water to be treated 8. In the floc generation state shown in A of FIG. 4, although the particle diameter is 1 [mm] or less, the flocs 68 larger than the flocs 68 shown in A of FIG. 3 are generated. When the flocs 68 enter and exit the measurement region 18, the scattering state of light changes, so that the output signal Do changes. Therefore, the entry and exit of the flocs 68 can be comprehended based on the change of the output signal Do.

The waveform of the output signal Do is different in shape depending on the particle diameter of the flocs 68 and the number of flocs in the measurement region 13.

It is assumed that a first water to be treated contains the flocs 68 with the particle diameter of r [mm] and that a second water to be treated whose a turbidity with the SS is the same as that of the first water to be treated contains the flocs 68 having the particle diameter of 2r [mm]. It is assumed that $N_r$ is the number of particles of the flocs 68 with the particle diameter of r [mm] and that $N_{2r}$ is the number of particles of the flocs 68 with the particle diameter of 2r [mm]. Since the turbidity with the SS by the flocs 68 is constant, the particle number N is proportional to a value obtained by dividing the turbidity with the SS by a unit volume, and can be represented by $$N_r:N_{2r}=(\pi r^3)^{-1}:\{\pi(2r)^3\}^{-1}=8:1 \qquad (1).$$

On the other hand, when $S_r$ is the surface area generating the scattered light of the flocs 68 with the particle diameter of r [mm] and $S_{2r}$ is the surface area generating the scattered light of the flocs 68 with the particle diameter of 2r [mm], the surface areas can be represented by $$S_r:S_{2r}=\pi r^2:\pi(2r)^2=1:4 \qquad (2).$$

On the assumption that the intensity of the scattered light is represented by the sum of the particle surface areas in the measurement region 18, the average value of the intensity of the scattered light generated by the water to be treated with the particle diameter 2r [mm] and the particle number $N_{2r}$ is represented by $$\text{Average value}=N_{2r}\times S_{2r}=N_r/8\times 4S_r=\tfrac{1}{2}\times N_r S_r. \qquad (3).$$

Therefore, the average value is a half of an average value of the intensity of the scattered light generated by the water to be treated with the particle diameter r [mm] and the particle number $N_r$.

In this regard, a change in the level of the average intensity of the scattered light is proportional to a change in the laser-applied particle surface area of the particles entering and exiting the measurement region 18. Therefore, when one particle with the particle diameter 2r [mm] enters and exits the measurement region 18, the change in the level of the average intensity of the scattered light is four times as large as the change in the level of the average intensity of the scattered light when one particle with the particle diameter r [mm] enters and exits the measurement region 18.

B of FIG. 3 shows an example of a detection waveform of the output signal Do in the generation state shown in A of FIG. 3, and B of FIG. 4 shows an example of a detection waveform of the output signal Do in the generation state shown in A of FIG. 4. In B of FIG. 3 and B of FIG. 4, amplitudes AW of waveforms represent changes in the scattered lights due to the entry and exit of the flocs 68.

In the generation state of A of FIG. 3, since the particles of the flocs 68 are small, the amplitude AW of the waveform is small as shown in B of FIG. 3 and the change in the scattered light is small. In contrast, in the generation state of A of FIG. 4, since the particles of the flocs 68 are large, the amplitude AW of the waveform is large as shown in B of FIG. 4 and the change in the scattered light is large.

[Attenuation of Scattered Light]

In a transmission space transmitting the scattered light to the scattered-light receiving part 12, the scattered light generated in the measurement region 18 strikes the particles present in the transmission space and attenuates due to secondary scattering. The intensity of the scattered light reaching the scattered-light receiving part 12 is assumed to be proportional to a floc unoccupied volume in the transmission space (the volume of the space without the flocs 68). In this case, magnitude of attenuation is affected by unoccupied volumes $V_r$, $V_{2r}$ to a volume $V_d$ of a transmission space from the measurement region 18 to the scattered-light receiving part 12.

The space without the flocs 68 can be obtained from the complement of the particle volume present in the space. If the floc unoccupied volume is $V_r$ when the particle diameter of the flocs 68 is r [mm] and the floc unoccupied volume is $V_{2r}$ when the particle diameter is 2r [mm], the volumes can be represented by $$V_r:V_{2r}=(V_d-dv_r\times N_r):(V_d-dv_{2r}\times N_{2r}) \qquad (4).$$

A volume of each of the flocs 68 is denoted by $dv_r$ and $dv_{2r}$, which can be represented by $$dv_r:dv_{2r}=\pi r^3:\pi(2r)^3=1:8 \qquad (5).$$

Since the intensity of the scattered light reaching the scattered-light receiving part 12 is proportional to the intensity of the scattered light generated in the measurement region 13 multiplied by an attenuation factor, and since the intensity of the generated scattered light is assumed to be proportional to the surface areas $S_r$, $S_{2r}$ of the flocs 68, change amounts $\Delta P_r$, $\Delta P_{2r}$ of the light reception level generated by one particle entering and exiting the measurement region 18 are as follows:

$$\begin{aligned}\Delta P_r:\Delta P_{2r} &= S_r\times(V_d-dv_r\times N_r):S_{2r}\times(V_d-dv_{2r}\times N_{2r}) \\ &= S_r\times(V_d-dv_r\times N_r):4S_r\times(V_d-8dv_r\times 8^{-1}N_r) \\ &= S_r\times(V_d-dv_r\times N_r):4S_r\times(V_d-dv_r\times N_r) \\ &= 1:4 \\ &= r^2:(2r)^2.\end{aligned} \qquad (6)$$

Eq. (6) represents that the change amounts $\Delta P_r$, $\Delta P_{2r}$ of the light reception level generated by the particle entering and exiting the measurement region 18 change in proportion to the square of the particle diameter of the floc 68 to be detected. Therefore, as the flocculation progresses and the particle diameter of flocs becomes larger, the occurrence frequency of large changes in the light reception level increases.

[Signal Change of Output Signal Do]

Figure 5:
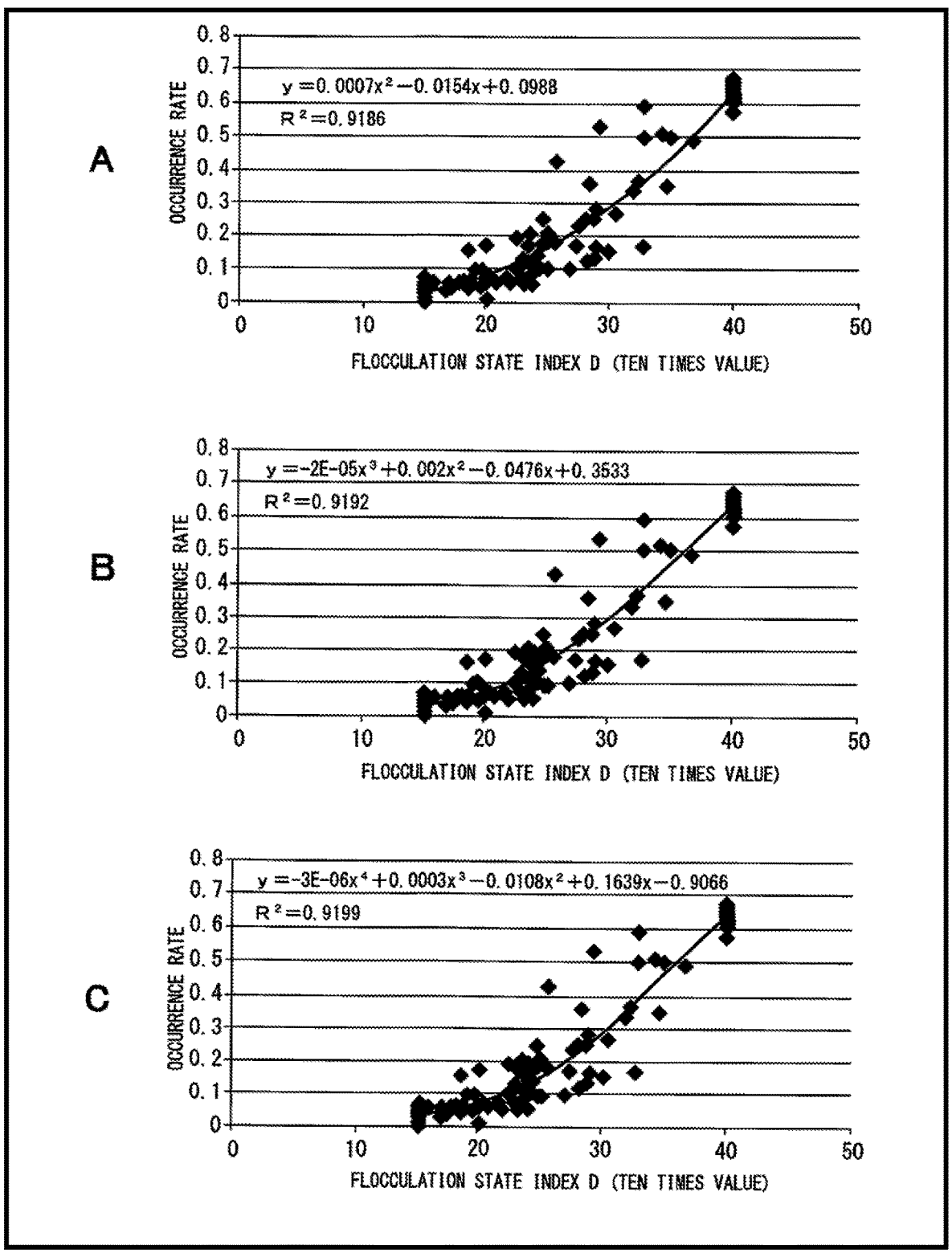
FIG. 5 is a diagram of an example of correlation between an amplitude occurrence rate of an output signal and a flocculation state index.

A of FIG. 5 is a graph acquired by aggregating the probability (occurrence rate) of appearance of large amplitude in the output signal Do. A measurement voltage range of this large amplitude is set to 200 [mV] to 1800 [mV] on the assumption of the change due to the entry and exit of the flocs 68. The occurrence rate was aggregated per minute (30 samples). For the measurement, samples with a known flocculation state were used. The flocculation state of each sample is classified by a flocculation state index. D indicative of the flocculation state into D0, D1, D2 . . . Dn. The flocculation state index D is related to a particle diameter Df of flocs in the samples, and the particle diameter Df of flocs in the samples of D1 to D4 is approximately as follows:

D1: Df=0.3 to 0.5 [mm];
D2: Df=0.5 to 0.75 [mm];
D3: Df=0.75 to 1.0 [mm]; and
D4: Df=1.0 to 1.25 [mm].

The horizontal axis of the graph shown in A of FIG. 5 indicates the value of the flocculation state index D increased by 10 times. Therefore, "10", "20", "30", and "40" on the horizontal axis indicate "D1", "D2", "D3", and "D4", respectively.

A quadratic curve shown in A of FIG. 5 is a curve when a correlation value ($R^2$ value) is the highest with respect to the aggregating result. The relationship between the occurrence rate (y) and a value (x) ten times as large as the flocculation state index B is $y=0.0007x^2-0.0154x+0.0988$, and the correlation value $R^2$ is 0.9186.

The relationship between the occurrence rate of the amplitude AW and the value ten times as large as the flocculation state index Q is a quadratic function. If the value ten times as large as the flocculation state index D on the horizontal axis is in a proportional relation with the particle diameter Df, the aggregating result shown in A of FIG. 5 consists with a logic represented by Eq. (6) described above.

If the particle diameter of the flocs 68 is a size falling within the range of the measurement region 18, a correlation exists between the probability (occurrence rate) of appearance of large amplitude in the output signal Do and the flocculation state index D, and therefore, the flocculation state index D of the water to be treated and the particle diameter Dr of the flocs 68 can be estimated by detecting the occurrence rate of the amplitude AW.

It is noted that A of FIG. 5 shows a result of quadratic-curve processing executed by performing quadratic approximation of measurement data based on theory. This is not a limitation, and cubic or higher-order approximation of measurement data may be performed for processing with a cubic or higher-order curve. B of FIG. 5 shows a result of cubic-curve processing executed by performing cubic approximation of measurement data. In this cubic approximation, the relationship between the occurrence rate (y) and the value (s) ten times as large as the flocculation state index D can be represented by $y=-2\times10^{-5}x^3+0.002x^2-0.0476x+3533$, and the correlation value $R^2$ is 0.9192.

C of FIG. 5 shows a result of quartic-curve processing executed by performing quartic approximation of measurement data. In this quartic approximation, the relationship between the occurrence rate (y) and the value; (x) ten times as large as the flocculation state index B can be represented by $y=-3\times10^{-6}x^4+0.0003x^3-0.01018x^2+0.1639x-0.9066$, and the correlation value $R^2$ is 0.9199.

As compared to the quadratic approximation, the correlation value $R^2$ increases from 0.918 to 0.919 in the cubic approximation and the correlation value $R^2$ increases from 0.918 to 0.320 in the quartic approximation. By using the cubic or quartic approximation, sub-elements related to light transmission/reception sensitivity such as slight transparency of the flocs 68 can be dealt with.

As shown in A to C of FIG. 5, when the flocculation state index D is small in the water to be treated 8, the occurrence rate of the amplitude of the output signal Do is low, and as the flocculation state index D rises, the occurrence rate of the amplitude of the output signal Do increases. Therefore, the flocculation state can be determined based on the occurrence rate of the amplitude of the output signal Do.

(2) Second Measurement Principle

In a second measurement principle, it is assumed that measurement is performed in the water to be treated 8 in which flocs having a particle diameter larger than the diameter of the measurement region 18 enter and exit the measurement region 18. Therefore, the second measurement principle covers the water to be treated 8 in which flocs exceeding the diameter of the measurement region 18 coexist.

[Measurement Principle when Flocs Exceeding Diameter of Measurement Region 18 Coexist]

When the floc 68 having a particle diameter exceeding the diameter of the measurement region 18 exists, a case that the floc 68 cannot entirely be accommodated in the measurement region 18 occurs. In this case, since the scattered light is generated from the entire measurement region 18, the scattered light and the amplitude thereof are saturated. Therefore, it becomes difficult to determine the particle diameter from the amplitude of the scattered light.

Figure 6:
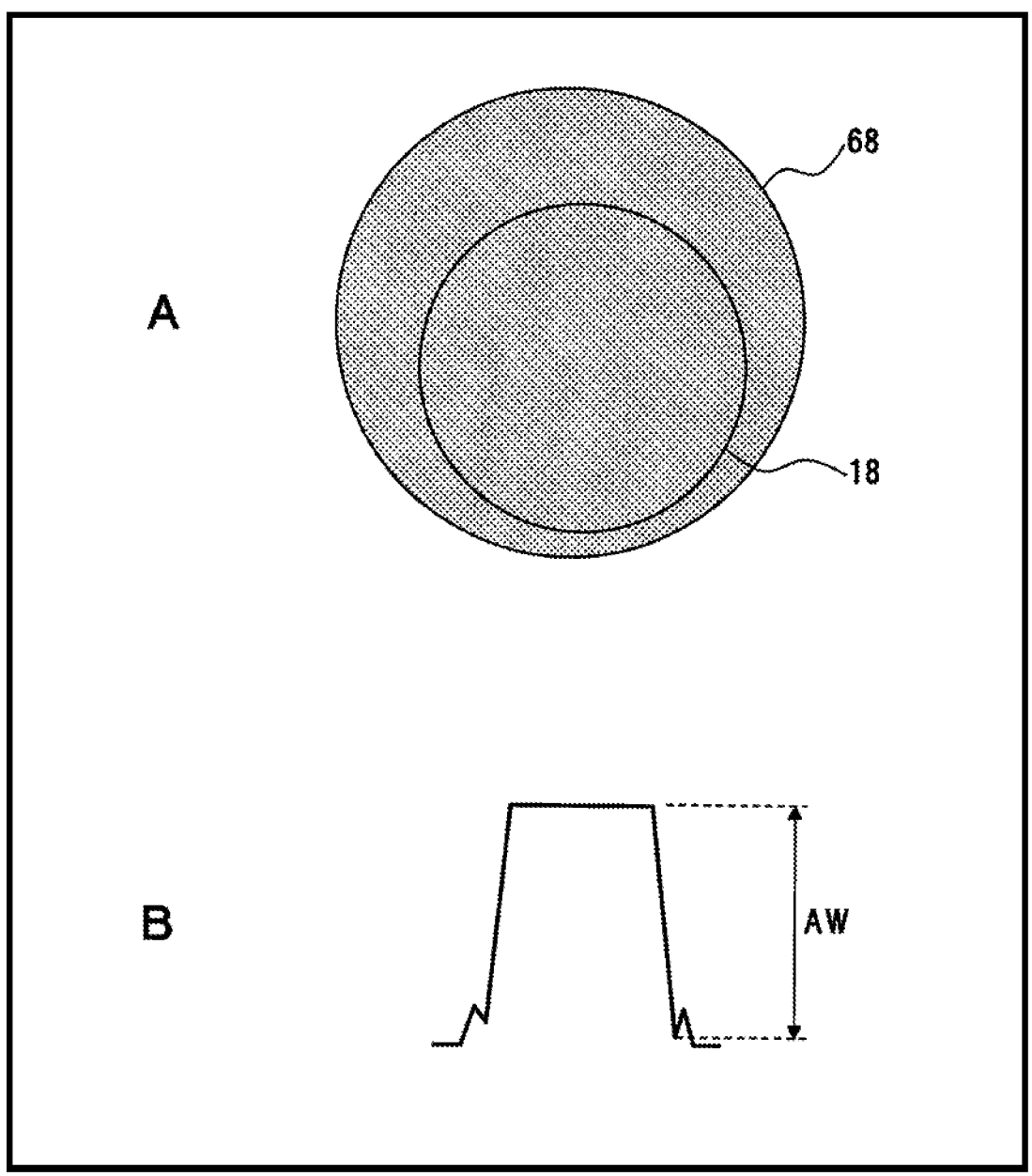
FIG. 6 is a diagram of examples of a floc generation state and a detection waveform of an output signal.
Figure 7:
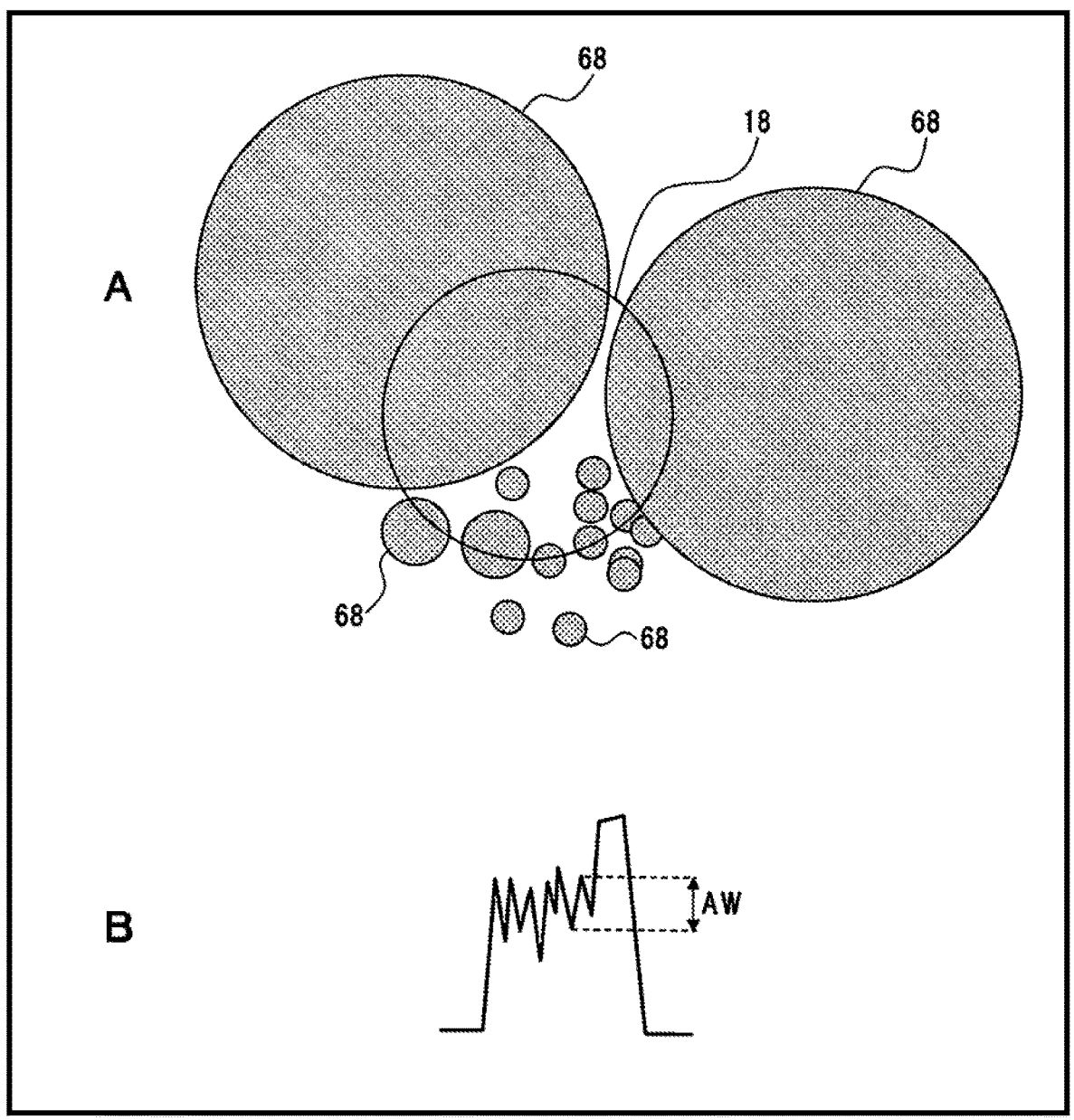
FIG. 7 is a diagram of examples of a floc generation state and a detection waveform of an output signal.

A of FIG. 6 and A of FIG. 7 show examples of generation states of a floc or flocs of 1 [mm] or more. A of FIG. 6 shows an example when a portion of a particle enters the whole application region and A of FIG. 7 shows an example when particles present in a particle gap enter and exit a detection region. B of FIG. 6 shows an example of a detection waveform of the output signal Do in the generation state shown in A of FIG. 6, and B of FIG. 7 shows an example of a detection waveform of the output signal Do in the generation state shown in A of FIG. 7. If the measurement region 18 has a circular shape with a diameter of about 1 [mm] and the flocs 68 grow larger than 1 [mm] in particle diameter, as shown in A of FIG. 6, a case that a portion of the floc 68 occupies the entire measurement region 18 occurs. In such the occurrence state, as shown in B of FIG. 6, the scattered light is saturated, and the amplitude AW of the waveform is saturated. Therefore, the upper limit of the amplitude AW of the waveform is the saturated value of the scattered light.

For example, movement of the floc 68 causes a shift to a state shown in A of FIG. 7. When the particle diameter of the flocs 68 is large, a relatively large gap is formed between the adjacent flocs 68 as compared to when the particle diameter is small. Therefore, in the state shown in A of FIG. 7, the small flocs 68 present in the gap between the large flocs 68 enter and exit the measurement region 18, so that the intensity of the output signal Do changes as shown in B of FIG. 7, for example, and the amplitude AW forms a large waveform. Therefore, by aggregating the amplitude AW of the waveform, particle diameter information of the flocs 68 in the gap between the large flocs 63 can be acquired.

Figure 8:
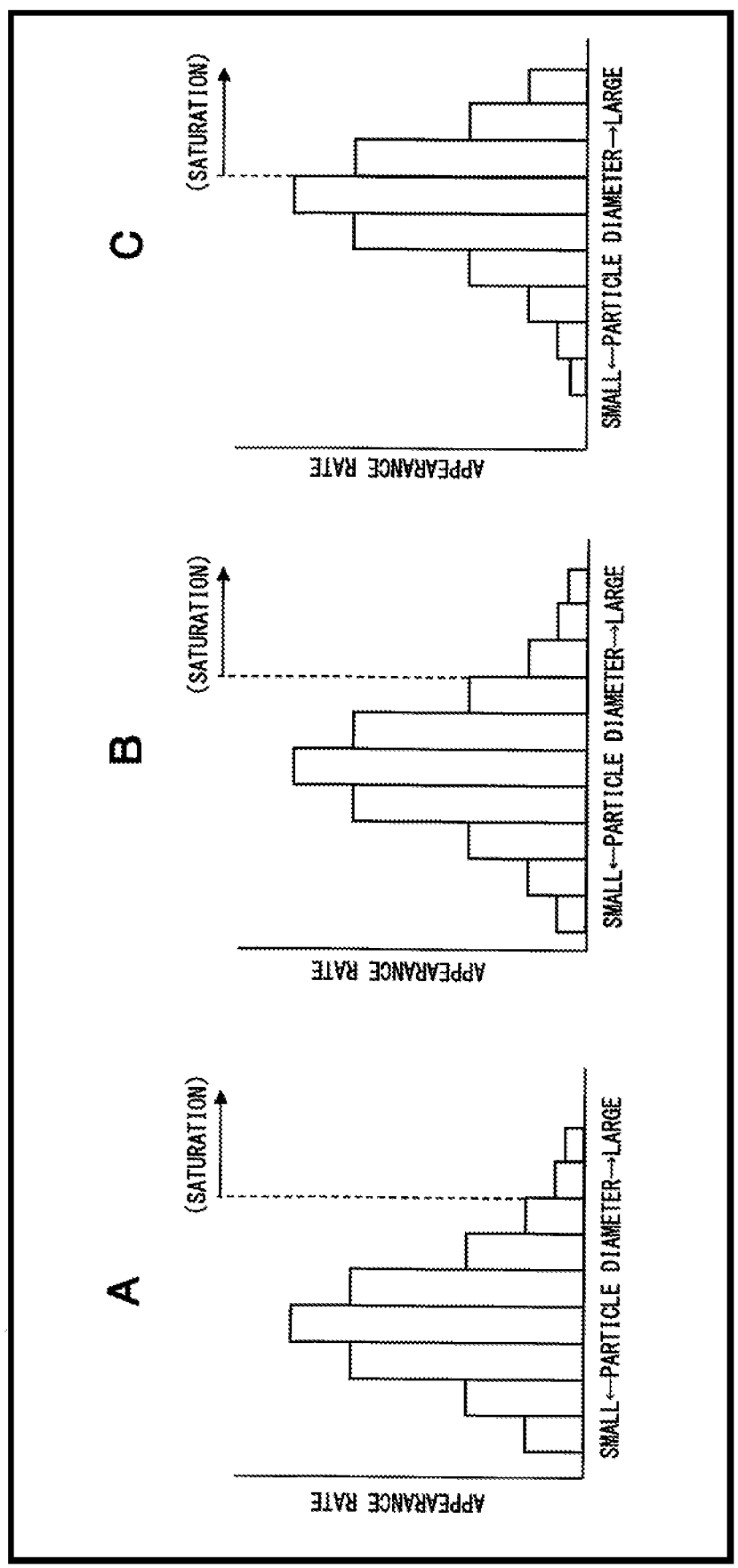
FIG. 8 is a diagram of an example of a floc appearance rate.

In the generation state of the flocs 63 shown in A and B of FIG. 7, if the appearance rate of the amplitude due to the entry and exit of flocs 63 is monitored for a certain period and the monitoring results are aggregated, the appearance rates of the flocs 68 against respective particle diameters are assumed to become a normal distribution as shown in A to C of FIG. 8. A of FIG. 8 is an example of distribution when the flocculation level is low; B of FIG. 8 is an example of distribution when the flocculation level is medium; C of FIG. 8 is an example of distribution when the flocculation level is high; and as flocculation progresses, the particle diameter of the flocs 63 becomes larger. If the particle diameter of the certain flocs 68 exceeds a certain magnitude, the amplitude AW of the waveform is saturated. Therefore, under the assumption that the appearance rates of the flocs 68 against the respective particle diameters become the normal distribution, the flocculation state can be evaluated by measuring (1) the particle diameter with the highest appearance rate, (2) the appearance rate against the particle diameter in a specific range, (3) the particle diameter with the highest appearance rate and the appearance rate against the particle diameter in a specific range, or the like. If a low flocculation state as shown in A of FIG. 8 progresses into a high flocculation state as shown in C of FIG. 8, a time when the amplitude AW of the waveform is saturated becomes long due to the entry and exit of the larger flocs 68 as the number of flocs decreases; however, by making the aggregating time longer, inconveniences due to the decrease in floc number and the saturation of the amplitude AW of the waveform can be eliminated.

<Relationship between Inflection Point Occurrence Frequency of Output Signal Do and Flocculation State Index D>

The following experiment will be described in relation to a certain relationship between the occurrence frequency of the first and second inflection points of the output signal Do and the flocculation state as described in "Measurement Principle of Flocculation State According to Amplitude Detection".

[Experimental Conditions]

A flocculation state is measured for the water to be treated 8 containing 3 to 4% of inorganic fine particles including kaolin etc. as SS and acquired results are evaluated. For the measurement, the light emission conditions of the laser-light applying part 10 were set to the light-emitting time: 0.2 seconds at a time and the light-emitting interval: 2 seconds. The data aggregating time was ten seconds and the data collection time was four hours. A level of flocculation of the water to be treated 8 is known and is each of seven levels shown below.

Level 0: level corresponding to D0 of the flocculation state index D

Level 1: level corresponding to D1 of the flocculation state index D

Level 2: level corresponding to D2 of the flocculation state index D and close to D1 (hereinafter referred to as "D2A")

Level 3: level corresponding to D2 of the flocculation state index D and close to D3 (hereinafter referred to as "D2B")

Level 4: level corresponding to D3 of the flocculation state index D and close to D2 (hereinafter referred to as "D3A")

Level 5: level corresponding to D3 of the flocculation state index D and close to D4 (hereinafter referred to as "D3B")

Level 6: level corresponding to D4 of the flocculation state index D

[Experimental Result]

Figure 9:
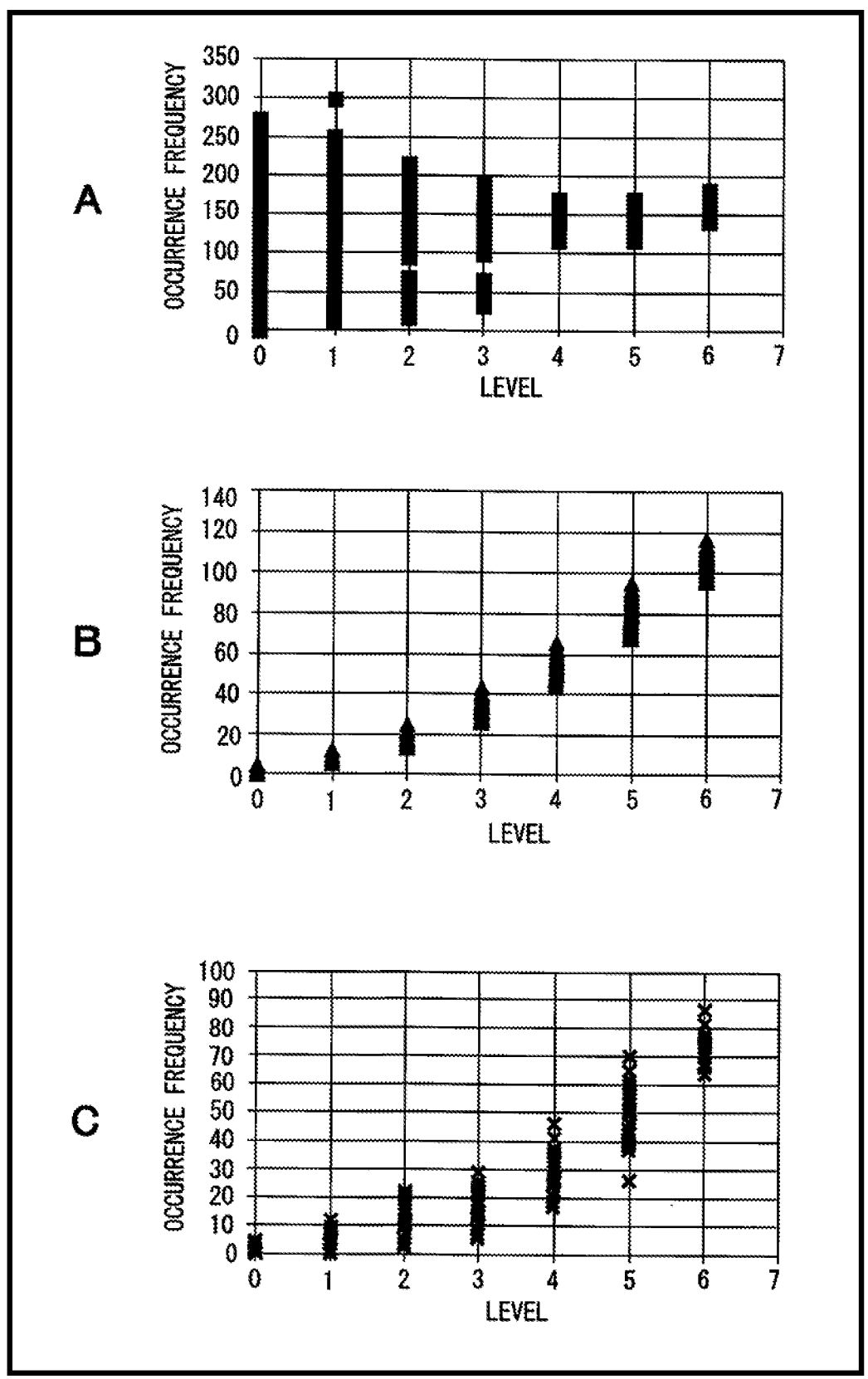
FIG. 9 is a diagram of an occurrence frequency of amplitude.
Figure 10:
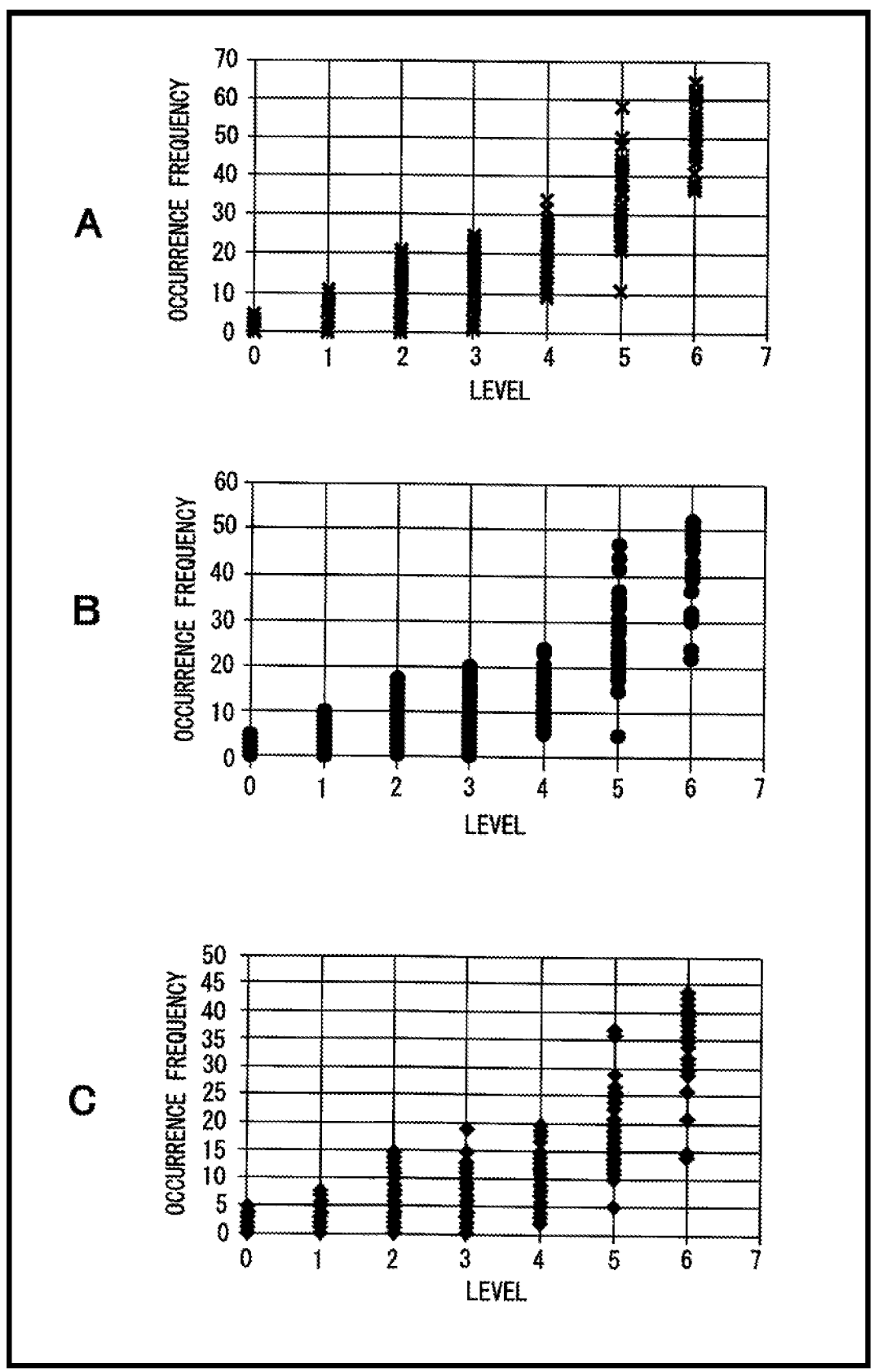
FIG. 10 is a diagram of an occurrence frequency of amplitude.

A to C or FIG. 9 and A to C of FIG. 10 show the occurrence frequency of the amplitude of the output signal Do of water to be treated different in flocculation level for each of certain amplitude ranges. A of FIG. 3 shows the occurrence frequency of the amplitude of 0 [mV] or more and less than 200 [mV]; B of FIG. 3 shows the occurrence frequency of the amplitude of 200 [mV] or more and less than 400 [mV]; and C of FIG. 9 shows the occurrence frequency of the amplitude of 400 [mV] or more and less than 600 [mV]. A of FIG. 10 shows the occurrence frequency of the amplitude of 600 [mV]; or more and less than 800 [mV]; B of FIG. 10 shows the occurrence frequency of the amplitude of 800 [mV] or more and less than 1000 [mV]; and C of FIG. 10 shows the occurrence frequency of the amplitude of 1000 [mV] or more.

Figure 11:
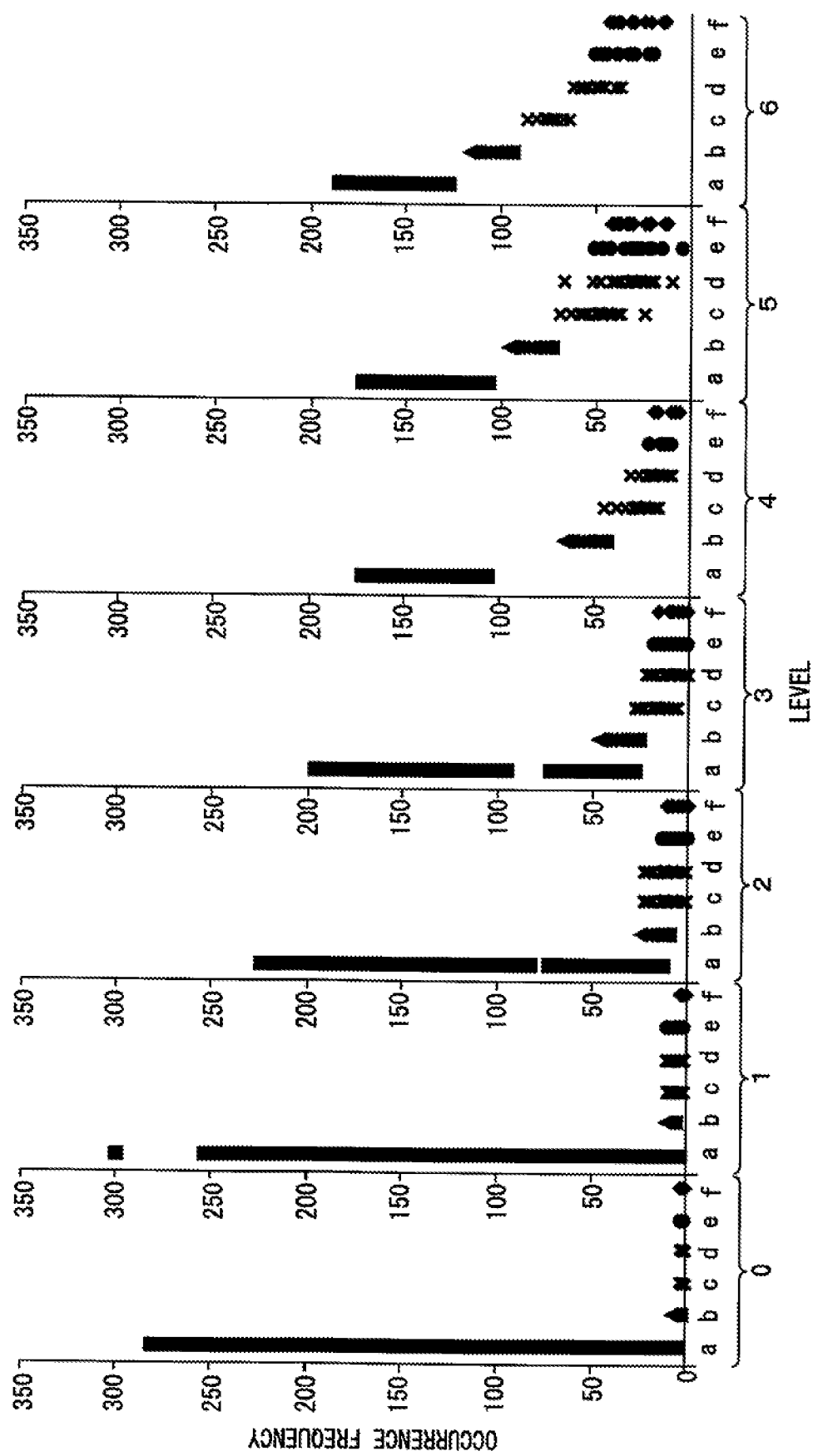
FIG. 11 is a diagram of the occurrence frequencies shown in FIGS. 9 and 10 classified by magnitude of amplitude.

FIG. 11 shows the occurrence frequency shown in FIGS. 9 and 10 classified into respective amplitude ranges indicated by a to f as follows:

a: amplitude of 0 [mV] or more and less than 200 [mV];
b: amplitude of 200 [mV] or more and less than 400 [mV];
c: amplitude of 400 [mV] or more and less than 600 [mV];
d: amplitude of 600 [mV] or more and less than 800 [mV];
e: amplitude of 800 [mV] or more and less than 1000 [mV]; and
f: amplitude of 1000 [mV] or more.

In the case of the signal of the amplitude of 0 [mV] or more; and less than 200 [mV], as shown in A of FIG. 9, the occurrence frequency of amplitude becomes higher as the water comes closer to a flocculation failure state (i.e., the state of level 0) and the occurrence frequency of amplitude is dispersed. In contrast, in the state of favorable flocculation with large flocs (i.e., the state of level 6), the dispersion of the occurrence frequency of amplitude becomes small.

As compared to the signal of the amplitude of 0 [mV] or more and less than 200 [mV]in the ease of the signal of the amplitude of 200 [mV] or more and less than 400 [mV], as shown in B of FIG. 9, the occurrence frequency of amplitude becomes higher as the water comes closer to the state of favorable flocculation with large flocs. As shown in FIG. 11, at each of levels 0 to 6, the dispersion of the signal is smaller as compared to the signal of the amplitude of 0 [mV] or more and less than 200 [mV]. A tendency similar to the signal of the amplitude of 200 [mV] or more and less than 400 [mV] is also recognized in the signal of the amplitude of 400 [mV] or more.

By averaging and graphically showing the occurrence frequency of the amplitude of 200 [mV] or more and less than 400 [mV] for each of the levels 0 to 6 of flocculation, the levels can be shown in Table 1 as follows.

TABLE 1

| FLOCCULATION STATE INDEX D | LEVEL | OCCURRENCE FREQUENCY [NUMBER OF TIMES] |
| --- | --- | --- |
| D0 | 0 | 2.6~5.2 |
| D1 | 1 | 5.2~12.9 |
| D2A | 2 | 12.9~25.7 |
| D2B | 3 | 25.7~43.7 |
| D3A | 4 | 43.7~66.7 |
| D3B | 5 | 66.7~94.9 |
| D4 | 6 | 94.9~ |

By averaging and graphically showing the occurrence frequency of the amplitude of 400 [mV] or more and less than 600 [mV] for each of the levels 0 to 6 of flocculation, the levels can be shown in Table 2 as follows.

TABLE 2

| FLOCCULATION STATE INDEX D | LEVEL | OCCURRENCE FREQUENCY [NUMBER OF TIMES] |
| --- | --- | --- |
| D0 | 0 | 1.5~3.3 |
| D1 | 1 | 3.3~8.8 |
| D2A | 2 | 8.8~17.9 |
| D2B | 3 | 17.9~30.6 |
| D3A | 4 | 30.6~47 |
| D3B | 5 | 47~67 |
| D4 | 6 | 67~ |

Similar to the occurrence frequency of the amplitude of 200 [mV] or more and less than 400 [mV] and the occurrence frequency of the amplitude of 400 [mV] or more and less than 600 [mV], the levels 0 to 6 of flocculation can be represented by using the occurrence frequency of the amplitude of 600 [mV] or more. Therefore, the flocculation state index D of the water to be treated 8 can be determined by using the occurrence frequency of the amplitude of 200 [mV] or more. Thus, flocculation states can be determined based on the flocculation state index D and a flocculation state can be controlled based on these flocculation states.

In this experiment, the occurrence tendency of the occurrence frequency changes at 200 [mV] serving as a threshold value. In other words, the dispersion is large at the amplitude of less than 200 [mV], while the dispersion is small at the amplitude of 200 [mV] or more. At the amplitude of 200 [mV] or more, the occurrence frequency of amplitude increases as the flocculation progresses, and a correlation exists between the occurrence frequency and the flocculation state, while no such a correlation is recognized at the amplitude less than 200 [mV]. The amplitude used for measuring the flocculation state may be any amplitude equal to or greater than the threshold value at which the occurrence tendency changes as described above, and is not limited to the amplitude of 200 [mV] or more.

<Measurement Principle of Flocculation State According to Minimum Value Detection>

In the water to be treated 8 in the flocculation tank 6, the flocculation treatment is promoted by dosing of a flocculant and stirring. When the fine colloidal particles move to the measurement region 18 due to this stirring, the scattered light from the fine colloidal particles varies. This variation period can be estimated and approximated from the number of collisions occurring between the measurement region 18 considered as a particle and the fine colloidal particles. When the measurement region 13 is approximated to a sphere having a radius R and the fine colloidal particles are approximated to spheres having a radius r, the collision cross section Qo can be represented by $$Q_o = \pi(R+r)^2 \quad (7).$$

As is clear from this equation, the collision cross section Qo is proportional to the square of the addition value of the radius R and the radius r.

In particular, when a cross-sectional area perpendicular to a constant flow direction in which particles having the average radius r at a colloidal particle density N [particles/m$^3$] pass through the measurement region 18 having the radius R at an average speed v [m/s] is assumed, the number of times ν of the fine colloidal particles entering the measurement region 18 per unit time can be represented by $$\nu = NQ_o v \quad (8).$$

Similarly, variation also occurs when the fin colloidal particles, exit the measurement region 18, and the period of the value acquired by differentiating the scattered light intensity is a value that is twice the number of times ν.

On the assumption that the scattered light intensity is proportional to the nth power of the particle diameter of the fine colloidal particles, when the multiple scattering is ignored, a variation A of the scattered light intensity due to movement of one of the fine colloidal particles is as follows:

$$A = A_o r^n \quad (9).$$

Ao is a constant depending on a measurement system and is a value calibrated by using a standard sample.

The fine colloidal particles before flocculation have a small radius r and a large particle density N, so that a minute variation of the scattered light occurs in a short period.

Therefore, when the detection circuit 40 detects the modulation frequency component, the output waveform thereof can be subjected to the signal processing equivalent to passing through the bandpass filter 44 or a high-pass filter. Therefore, the cutoff frequency of the bandpass filter 44 can appropriately be selected so as to detect the output signal Do from which a variation component due to the modulation frequency component is removed.

The variation when colloid flocculated from the water to be treated 8 (flocculated colloid) enters and exits the measurement area 18 is larger and the average period of this variation is longer. If the product of the density of the flocculated colloid and the volume of the measurement region 18 is smaller than one, the minimum value of the output waveform after detection by the detection circuit 40 corresponds to the scattering of the non-flocculated colloid.

The output signal Do acquired by the detection circuit 40 includes signals due to the scattered light of the non-flocculated colloid and other scattered lights, and these signals can be classified into the scattered light due to the flocculated colloid and the scattered light due to the non-flocculated colloid in the water to be treated 8 according to the signal amplitude level. Therefore, the signal component of the amplitude level corresponding to the scattered light due to the non-flocculated colloid can be extracted from the output signal Do so as to detect the flocculation state of the colloid as the treatment state of the water to be treated 8, and the flocculation state of the colloid can be comprehended.

<Output of Flocculation Index>

The laser light applied from the laser-light emitting part 20 strikes the flocs 68 present on the optical path of the laser-light and generates the scattered light. On the assumption that the average particle density from the point of generation of the scattered light to the scattered-light receiving part 12 is substantially constant, when the density of the flocs is high (when the flocs are small), a change in distance between a particle and a light-emitting surface is small in terms of the scattered light, and the amplitude of the output signal Do becomes smaller as compared to when the large flocs are generated. Conversely, when the flocs are large, a change in distance between a particle and a light-emitting surface is large, and the amplitude of the output signal Do becomes larger as compared to the case of the small flocs.

Such a relationship is established in a state of a high floc density such as when the laser light emitted from the laser-light applying part 10 strikes the flocs immediately after emission. In this case, the minimum value of the signal intensity has information on the size of the flocs, rather than the turbidity among the flocs. In other words, when the flocs are large, the application area becomes larger, so that the level of the scattered light generated by the laser light striking the floc surface becomes higher, and the enlargement of the flocs expands gaps between the flocs and increases the opportunities that the level of the scattered light becomes higher. Conversely, when the flocs are small and the density is high, the scattered light level becomes lower due to a reduction in the surface area of the flocs irradiated by the scattered light, and the gaps between the flocs is smaller, so that an attenuation rate of the scattered light before reaching the scattered-light receiving part 12 becomes higher and that the light reception level becomes lower. Therefore, the amplitude level and the level of the minimum value are as shown in Table 3.

TABLE 3

| CASE | MINIMUM VALUE LEVEL | AMPLITUDE LEVEL | FLOCCULATION INDEX |
|---|---|---|---|
| 1 | LOW | SMALL | LOW (TO INCREASE FLOCCULANT DOSING AMOUNT) |
| 2 | MEDIUM | LARGE | APPROPRIATE (TO MAINTAIN FLOCCULANT DOSING AMOUNT) |

TABLE 3-continued

| CASE | MINIMUM VALUE LEVEL | AMPLITUDE LEVEL | FLOCCULATION INDEX |
|---|---|---|---|
| 3 | HIGH | LARGE | EXCESSIVE (TO REDUCE FLOCCULANT DOSING AMOUNT) |
| 4 | HIGH | SMALL | LOW (TO INCREASE FLOCCULANT DOSING AMOUNT) |
| 5 | LOW | LARGE | APPROPRIATE OR EXCESSIVE [MEASURABLE STATE OF TURBIDITY AMONG FLOCS] |

According to Table 3, when the amplitude level of the output signal Do is equal to or greater than a certain value, it can be determined that the flocculant dosing amount is appropriate or excessive. In this case, "appropriate", "appropriate or excessive", or "excessive" as the flocculation index can be output and the flocculant dosing amount can be maintained or reduced.

When the amplitude level is less than the certain value, it can be determined that the flocculant dosing amount is small. In this case, "low" as the flocculation index can be output and the flocculant dosing amount can be increased. This amplitude level is an index corresponding to the probability (occurrence rate) of appearance of large amplitude in the output signal Do described above and the occurrence frequency of the amplitude of the output signal Do.

The flocculation index may be determined not only by determining that the flocculation is "low", "appropriate", "appropriate or excessive", or "excessive" according to the amplitude level, but also in combination with determination, according to the minimum value level of the output signal Do. By combining multiple measurement methods, the flocculation state can be determined in more detail.

The flocculation state can be determined while switching the dosing control according to the measurement of the amplitude level and the dosing control according to the measurement of the minimum value level. In this case, when the SS concentration is so high that it cannot be expected to detect a gap between the flocs and the flocculated floc concentration is high, the dosing may be controlled according to the amplitude level, and when the dosing can be controlled with the minimum value level as in Case 5 of Table 3, the control may be provided according to the minimum value level.

<Signal Processing and Signal Processing of Measurement Value>

Figure 12:
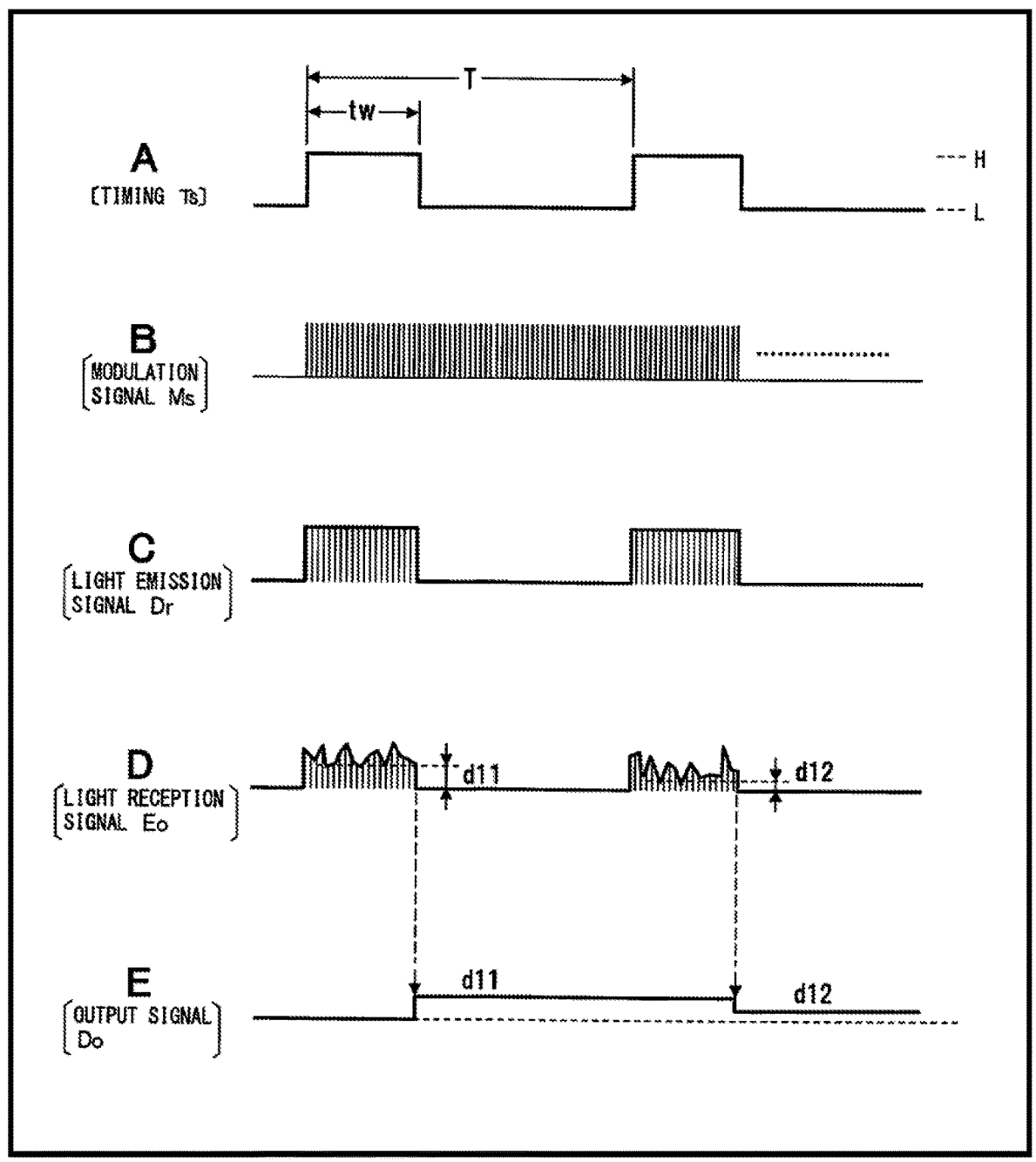
FIG. 12 is a diagram of examples of operation waveforms.

FIG. 12 shows processing of signals used for the monitoring. In this signal processing, a timing signal Ts is a pulse signal having a constant pulse width tw at an interval (period) of a constant time T as shown in A of FIG. 12. In this case, an H-level section (=pulse width tw) is the light-emitting time of the laser light, and an L-level section (=T−tw) is the non-light-emitting time of the laser light. For instance, T is set at 2 [seconds] and tw is set at 0.2 [seconds]. In this case, T minus tw (T−tw) may be set at 2 [seconds].

As shown in B of FIG. 12, the modulation signal Ms is a periodic signal having a constant frequency f and the same amplitude. The frequency f can be any frequency selected from 70 to 150 [kHz].

As shown in C of FIG. 12, the light emission signal Dr is an output signal of the AM modulation circuit 30 modulating the timing signal Ts with the modulation signal Ms. Specifically, the light emission signal Dr is a periodic signal with the modulation signal Ms superimposed in the pulse width tw of the H-level section of the timing signal Ts. Therefore, the light emission signal Dr is the periodic signal that varies with the amplitude of the modulation signal Ms at the pulse width tw and that intermits with the timing signal Ts.

By using the light emission signal Dr as described above, a laser light having a light-emitting form according to the light emission signal Dr can be acquired from the laser-emitting element 26.

When this laser light is applied to the measurement region IS from the laser-light applying part 10, a scattered light can be acquired from particles in the water to be treated 8 staying in the measurement region 18. This scattered light is received by the scattered-light receiving part 12.

Subsequently, through the photoelectric conversion of the photoelectric conversion circuit 38, a filtering process, and amplification, the light reception signal Eo is acquired on the output side of the amplifier 46 as shown in D of FIG. 12. The light reception signal Eo intermits with the timing signal Ts, has the frequency of the modulation signal Ms, and has amplitude of a level corresponding to the intensity of the scattered light.

When this light reception signal Eo is detected by the detection circuit 40, as shown in E of FIG. 12, the output signal Do intermitting with the timing signal Ts and having a direct-current level corresponding to the intensity of the scattered light can be acquired. In the signal processing of the light reception signal Eo, for example, the output of the bandpass filter 44 is half-wave rectified and detected, and the bottom peak of the detection output is then peak-held, so that the output signal Do is acquired.

Therefore, in the arithmetic circuit 48, the amplitude and the minimum value of the signal level described above are measured through the A/D conversion from the output signal Do.

<Process Procedure of Flocculation Monitoring>

Figure 13:
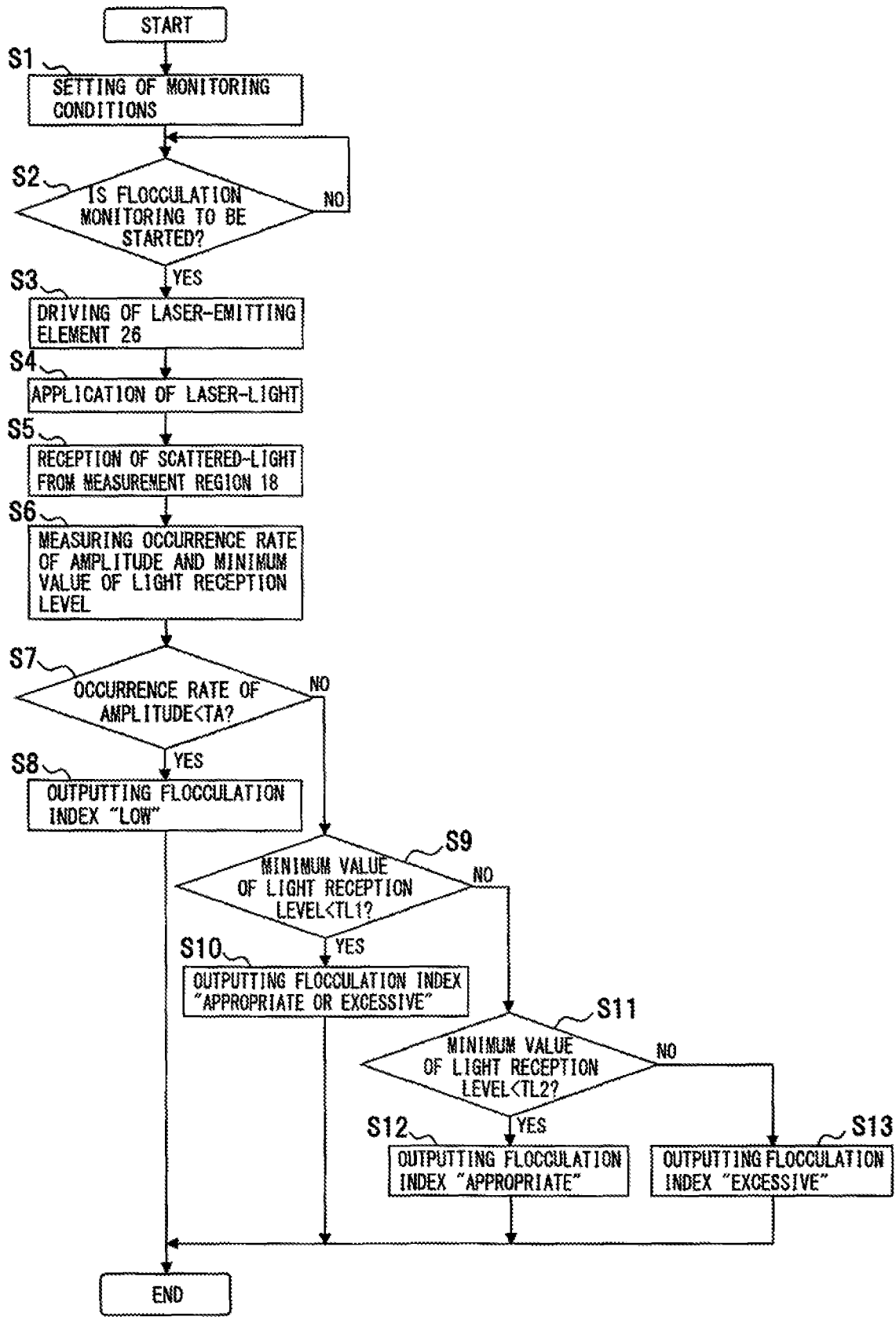
FIG. 13 is a flowchart of a process procedure of flocculation monitoring.

FIG. 13 shows an example of a process procedure of the flocculation monitoring. This process procedure is an example of a flocculation monitoring method of the present invention. This process procedure is executed by computing processing (information processing) including the processor 58 and the memory part 60 included in the arithmetic circuit 48.

In this process procedure, conditions of flocculation monitoring are set at a condition setting step (S1). In this condition setting, a threshold value TA, a threshold value TL1 and a threshold value TL2 are set, for example. The threshold value TA is for determining the magnitude of the amplitude level, the threshold value TL1 is for determining that the level of the output signal Do is equal to or lower than a low level or equal to or greater than a medium level, and the threshold value TL2 is for determining that the level of the output signal Do is equal to or less than the medium level or equal to or greater than a high level. The threshold values TL1, TL2 are set to satisfy as follows: threshold value TL1 <the threshold value TL2, and the threshold values TA, TL1, and TL2 are appropriately set depending on the turbidity with the SS of the water to be treated and the amplification factor of the signal in the photoelectric conversion circuit 38.

After this condition setting, it is determined whether flocculation monitoring is to be started (S2). When the monitoring is started (YES at S2), the procedure goes to a laser emission step to drive the laser-emitting element 26 (S3), and then goes to a laser-light application step (S4). At the laser-light application step, the laser light is applied to the measurement region 18 as described above.

At a scattered-light reception step (S5), as described above, the scattered light is received from the measurement region 18 and converted into the light reception signal having a level representative of the intensity of the scattered light.

At a signal processing step (S6), as described above, the occurrence rate of amplitude and the minimum value of the light reception level are measured. These measurement values are determined for each of the measurement values. The occurrence rate of amplitude may be measured as an occurrence frequency of amplitude.

It is determined whether the occurrence rate of amplitude is less than the threshold value TA (S7). If the occurrence rate of amplitude is less than the threshold value TA (YES at S7), the flocculation of water to be treated is at the low level, so that the flocculation index indicative of the "low" level is output (S8). From such a determination, Case 1 and Case 4 shown in Table 3 can be determined. Since the flocculation level is low, the control for increasing a dosing amount is provided under the output of such a flocculation index.

If the occurrence rate of amplitude is equal to or greater than the threshold value TA (NO at S7), the flocculation of water to be treated is at the appropriate level or the excessive level, and it is therefore determined whether the minimum value of the light reception level is less than the threshold value TL1 (S9).

If the minimum value of the light reception level is less than the threshold value TL1 (YES at S9), the turbidity with the SS among the flocs 68 is in a measurable state, and therefore, the flocculation index indicative of the "appropriate or excessive" level is output (S10). From such a determination, Case 5 shown in Table 3 can be determined. Since the turbidity with the SS among the flocs 68 is in the measurable state, the dosing control based on the minimum value of the light reception level is provided under the output of such a flocculation index.

If the minimum value of the light reception level is equal to or greater than the threshold value TL1 (NO at S9), it is determined whether the minimum value of the light reception level is less than the threshold value TL2 (S11).

If the minimum value of the light reception level is less than the threshold value TL2 YES at S11), the flocculation index indicative of the "appropriate" level is output (S12). From such a determination, Case 2 shown in Table 3 can be determined. The control for maintaining the dosing amount is provided under the output of such a flocculation index.

If the minimum value of the light reception level is equal to or greater than the threshold value TL2 (NO at S11), the flocculation index indicative of the "excess" level is output (S13). From such a determination, Case 3 shown in Table 3 can be determined. The control for reducing the dosing amount is provided under the output of such a flocculation index.

<Action and Effect of First Embodiments>

According to the first embodiment, the following actions and effects can be acquired.

(1) The arithmetic circuit 48 includes the amplitude detecting part 50 measuring the amplitude of the waveform from a change in the signal waveform of the output signal Do as well as the minimum value detecting part 52 measuring the minimum value, calculates an index based on the amplitude when the measured value of the amplitude detecting part 50 is equal to or greater than a certain value, and outputs the index related to flocculation together with the minimum value or by performing an arithmetic operation of the minimum value. With such a configuration, when the amplitude is large, it is determined that flocs due to a flocculation action are large. In other words, it is determined that the dosing amount is sufficient or slightly excessive. When the amplitude is small, it is determined that the flocs are small. In other words, it is determined that the dosing amount is slightly insufficient. With such a determination, the dosing amount can be controlled to an arbitrary state.

(2) In the measurement of the flocculation index with the minimum value measuring part 52, the measurement must be performed while no large floc is present in the measurement region 18, i.e., while only the SS component not taken into the flocs is present; however, by performing the measurement with the amplitude detecting part 50 or by combining the measurement with the minimum value detecting part 52 and the measurement with the amplitude detecting part 50, the flocculation state can be measured even when a large floc or large flocs are present in the measurement region 18.

(3) Since the amplitude detecting part 50 is included, the flocculation state can be measured even when a large floc or large flocs are present in the measurement region 18, so that the light-emitting time of the laser-emitting element 26 can be shortened to acquire a life-extending effect for the laser-emitting element 26. For example, the water to be treated can be measured with the light emitted for the light-emitting time t that is 0.2 [seconds] at intervals of the constant time T that is 2 [seconds].

(4) Although the index is calculated by using the amplitude of 200 [mV] or more in the embodiment, the measurement may be performed by using any specific amplitude equal to or greater than a threshold value, and the occurrence frequency of the specific amplitude equal to or greater than the threshold value tends to become higher as the flocculation progresses. The index related to flocculation can be acquired by using the occurrence rate or the occurrence frequency from any amplitude as long as the amplitude is equal to or greater than the threshold value and, even if a large amount of flocs is generated in the water to be treated during flocculation and the floc density becomes higher, the treatment state of the water to be treated can stably be measured. Additionally, when the measurement is performed by using all the amplitudes equal to or greater than the threshold value, the parameter of the occurrence frequency can be increased, so that the flocculation state can be measured in a short time. Consequently, the treatment state of the water to be treated during flocculation can accurately be comprehended in real time, and the flocculant dosing amount corresponding to the treatment state can be selected.

[Second Embodiment]

Figure 14:
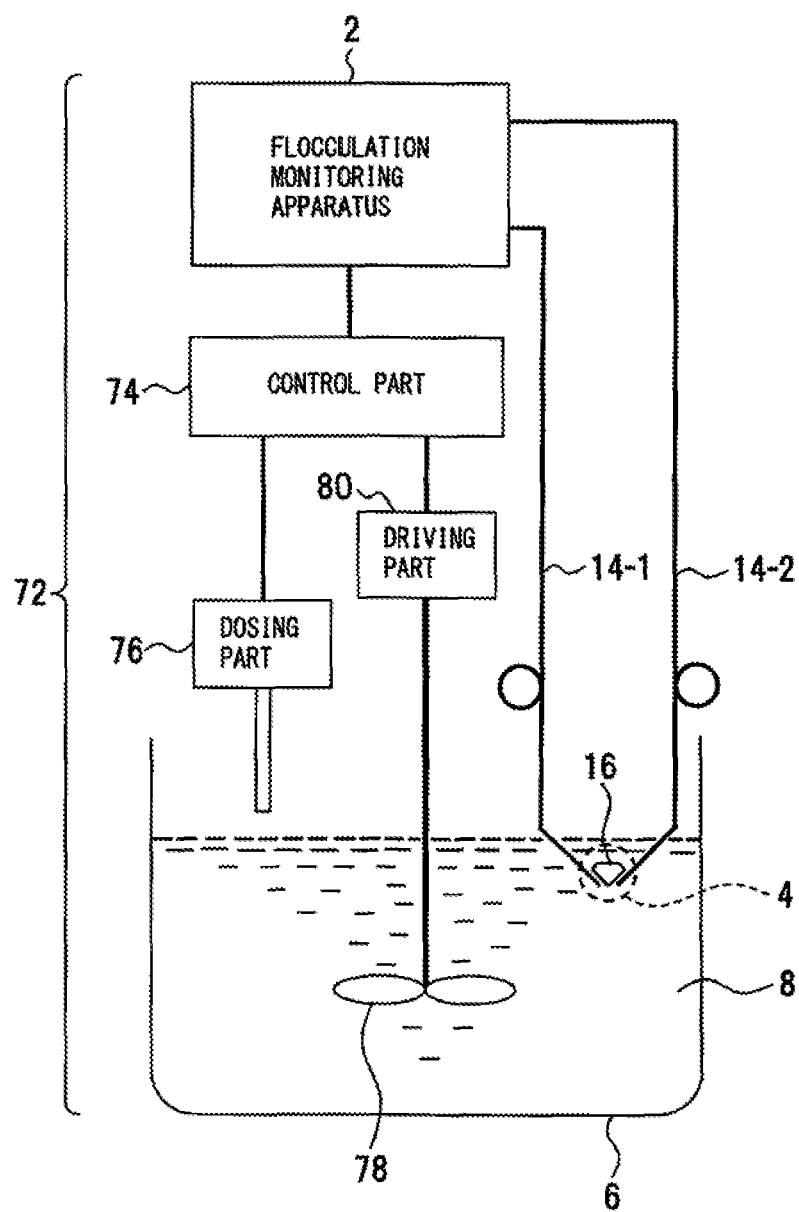
FIG. 14 is a diagram of an example of a flocculation system according to a second embodiment.

FIG. 14 shows a flocculation system according to a second embodiment. This flocculation system 72 is an example of flocculation treatment system using the flocculation monitoring apparatus 2 according to the first embodiment. In FIG. 14, the same portions as those of FIG. 1 are denoted by the same reference signs and description of the same portions will be omitted.

In the flocculation monitoring apparatus 2, a flocculation index of the water to be treated 8 undergoing the flocculation treatment in the flocculation tank 6 is calculated and provided to a control part 74. This flocculation index indicates the index of flocculation acquired from a treatment state of the water to be treated 8 subjected to the flocculation treatment in the flocculation tank 6.

This control part 74 controls the flocculation treatment of the water to be treated 8 in the flocculation tank 6 in terms of the flocculant dosing amount, the stirring control, etc. Flocculant is injected from a dosing part 76 into the water to be treated 8 in the flocculation tank 6. A stirrer 78 disposed in the flocculation tank 6 is driven by a driving part 80, and this driving is controlled by the control part 74.

The control part 74 is made up of a computer, for example, and the flocculant dosing amount is calculated by using the flocculation index provided from the flocculation monitoring apparatus 2.

<Flocculation Treatment of Flocculation System>

Figure 15:
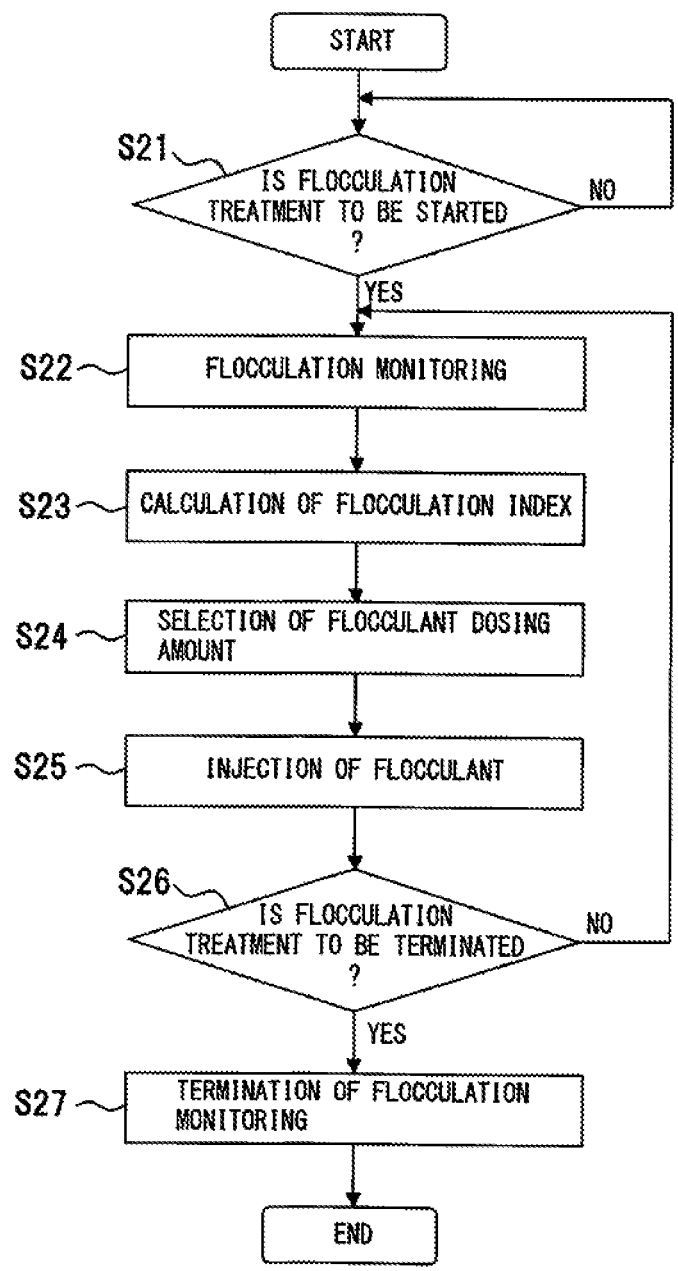
FIG. 15 is a flowchart of a process procedure of flocculation treatment.

FIG. 15 shows an example of a process procedure of the flocculation treatment. In this process procedure, it is determined whether the flocculation treatment is to fee started (S21), and the flocculation treatment is started according to the determination result. When the flocculation treatment is started (YES at S21), flocculation monitoring is performed for the treatment state of the water to be treated 8 in the flocculation tank 6 (S22). This flocculation monitoring is performed by the flocculation monitoring apparatus 2. Details of this treatment will be omitted. In the flocculation monitoring apparatus 2, the flocculation index indicative of the treatment state of the water to be treated 8 is calculated (S23) and provided to the control part 74 of the flocculation system 72.

When receiving the flocculation index, the control part 74 selects the flocculant dosing amount based on the flocculation index (S24). Consequently, the flocculant is injected from the dosing part 76 (S25).

Whether this flocculation treatment is to be terminated is monitored (S26) and, if the flocculation treatment is not to be terminated (NO at S26), the procedure returns to S22, and the flocculation treatment is continuously performed through the processes of S22 to S26.

If the flocculation treatment is to be terminated (YES at S26), the flocculation monitoring is terminated (S27) and the flocculation treatment is terminated.

<Action and Effect of Second Embodiment>

According to the second embodiment, the following functions and effects can be acquired.

(1) Since the state of the flocculation treatment is comprehended in real time and the flocculation index is generated from the measured value of the scattered light regardless of the presence of flocs and employed for the dosing control, the stable dosing control is realized.

(2) The flocculation conditions of the water to be treated and the flocculant dosing amount are obtained.

(3) The dosing amount can be optimized for the water to be treated and the stable flocculation treatment can be performed so as to improve flocculation efficiency.

(4) The compensation function of the flocculation system based on the measurement of the treatment state in the flocculation tank 6 can be maintained, the flocculant can be prevented from being excessively administered, so that an influence on the environmental burden is avoided, and the highly reliable flocculation treatment can be realized.

(5) Even in water to be treated in which a type of wastewater frequently changes, such as wastewater from a food manufacturing factory, an appropriate flocculation treatment corresponding to the type of wastewater can be performed to avoid an influence on the environmental burden.

[Other Embodiments]

(1) In the embodiments, the laser light emitted at predetermined time intervals and amplitude-modulated with a predetermined frequency is used; however, if the measurement of turbidity is prioritized without considering the life of the laser-emitting element, a laser light amplitude-modulated with a predetermined frequency may be used. In this case, multiple lowest level signals may be extracted from a continuous light reception signal at predetermined timing.

(2) In this embodiments, the bandpass filter 44 and the amplifier 46 may be realized from digital processing.

(3) In the embodiments, the water to be treated 8 whose the treatment state is monitored by the flocculation monitoring apparatus 2 is illustrated by purified water, industrial water, wastewater, etc.; however, the water to be treated 8 may be high concentration inorganic wastewater discharged from a quarry or drinking liquid such as fruit juice.

(4) In the embodiments, the flocculation tank 6 is included and the example that the flocculation index of the water to be treated 8 in the flocculation tank 6 is calculated is provided; however, in a system in which the flocculation treatment of the water to be treated 8 is performed by a line mixing apparatus included in a liquid feeding line for the water to be treated 8, a treated water tank may be provided for downstream of the line mixing apparatus, so that the flocculation monitoring may be performed. In particular, the water to be treated 8 subjected to the flocculation treatment may be stored in the treated water tank, so that the flocculation index of the water to be treated 8 may be calculated.

As described above, the most preferable embodiments etc. of the flocculation monitoring apparatus, the flocculation monitoring method, and the flocculation system of the present invention have been described. The present invention is not limited to the above description. The present invention can variously be modified and altered by those skilled in the art based on the spirit of the invention described in claims or disclosed in description of embodiments. These modifications and alterations obviously fall within the scope of the present invention.

INDUSTRIAL APPLICABILITY

According to the present invention, a treatment status of flocculation treatment of water to be treated such as purified water, industrial water, and wastewater can stable and accurately be comprehended and a contribution can be made to efficient flocculation treatment.

REFERENCE SIGNS LIST 2 flocculation monitoring apparatus
4 sensor part
6 flocculation tank
8 water to be treated
10 laser-light applying part
12 scattered-light receiving part
14-1 first optical fiber
14-2 second optical fiber
16 shielding member
18 measuring regions
20 laser-light emitting part
22-1 first supporting part
22-2 second supporting part
24 vertex portion 26 laser-emitting element
28 light-emitting circuit
30 AM modulation circuit
32 timing circuit
34 function generator
36 signal processing part
38 photoelectric conversion circuit
40 detection circuit
42 photodetector
44 bandpass filter
46 amplifier
48 arithmetic circuit
50 amplitude detecting part
52 minimum value detecting part
54 light emission control part
56 A/D
58 processor
60 memory part
62 program storage part
64 data recording part
66 RAM
72 flocculation system
74 control part
76 dosing part
78 stirrer
80 driving part

The invention claimed is:

1. A flocculation monitoring apparatus monitoring a treatment state of water to be treated that is subjected to a flocculation treatment, the apparatus comprising:
   a measurement-light applying part applying a measurement light to a measurement region in the water to be treated;
   a scattered-light receiving part receiving a scattered light due to particles of the water to be treated in the measurement region;
   a signal processing part that converts a light reception output from the scattered-light receiving part into an output signal indicating a level corresponding to the intensity of the scattered light; and
   a measurement value arithmetic part including an amplitude measuring means measuring a peak-to-peak amplitude of the output signal, the measurement value arithmetic part calculating an occurrence rate or occurrence frequency of a specific peak-to-peak amplitude by monitoring an appearance of the peak-to-peak amplitude and aggregating appearing peak-to-peak amplitudes, the measurement value arithmetic part calculating an index related to flocculation of the water to be treated, the index related to the flocculation indicating a particle diameter of flocs in the water to be treated, wherein
   the amplitude measuring means detects first inflection points at which the output signal changes from rising to falling and second inflection points at which the output signal changes from falling to rising, and measures a level difference between one of the first inflection points and one of the second inflection points that are adjacent to each other, as the peak-to-peak amplitude.

2. The flocculation monitoring apparatus according to claim 1, wherein the measurement value arithmetic part further includes a minimum value measuring means measuring from the output signal a minimum value of the signal and calculates the index related to the flocculation by using a measurement result of the amplitude measuring means or measurement results of the amplitude measuring means and the minimum value measuring means.

3. The flocculation monitoring apparatus according to claim 1, wherein
   the specific peak-to-peak amplitude has an occurrence frequency increasing as flocculation progresses.

4. The flocculation monitoring apparatus according to claim 2, wherein
   the specific peak-to-peak amplitude has an occurrence frequency increasing as flocculation progresses.

5. The flocculation monitoring apparatus according to claim 1, wherein the amplitude measuring means measures the number of occurrences of the peak-to-peak amplitude for each magnitude of the peak-to-peak amplitude.

6. The flocculation monitoring apparatus according to claim 1, wherein a magnitude of the specific peak-to-peak amplitude lies within a predetermined peak-to-peak amplitude range.

7. The flocculation monitoring apparatus according to claim 1, wherein the peak-to-peak amplitudes include the specific peak-to-peak amplitude of which a magnitude lies within a predetermined peak-to-peak amplitude range and another peak-to-peak amplitude of which a magnitude lies out of the predetermined peak-to-peak amplitude range.

8. The flocculation monitoring apparatus according to claim 1, wherein the amplitude measuring means detects an occurrence of the peak-to-peak amplitude by detecting said one of the first inflection points and said one of the second inflection points, which are adjacent to each other, and obtains the level difference between said one of the first inflection points and said one of the second inflection points to measure a magnitude of the occurring peak-to-peak amplitude.

9. A flocculation monitoring method of monitoring a treatment state of water to be treated that is subjected to a flocculation treatment, the method comprising:
   a measurement-light applying step of applying a measurement light to a measurement region in the water to be treated;
   a scattered-light receiving step of receiving a scattered light due to particles of the water to be treated in the measurement region;
   step of converting a light reception output of the scattered light into an output signal indicating a level corresponding to the intensity of the scattered light
   a signal processing step of extracting measurement values of the output signal; and
   a measurement value arithmetic step of detecting first inflection points at which the output signal changes from rising to falling and second inflection points at which the output signal changes from falling to rising from the measurement values of the output signal, measuring a level difference between one of the first inflection points and one of the second inflection points that are adjacent to each other, as a peak-to-peak amplitude of the output signal, calculating an occurrence rate or occurrence frequency of a specific peak-to-peak amplitude by monitoring an appearance of the peak-to-peak amplitude and aggregating appearing peak-to-peak amplitudes, and calculating an index related to flocculation of the water to be treated, the index related to the flocculation indicating a particle diameter of flocs in the water to be treated.

10. A flocculation system performing a flocculation treatment for water to be treated, the system comprising:
   a treated water tank storing the water to be treated;
   a flocculation monitoring means monitoring a treatment state of the water to be treated in the treated water tank; and a dosing means injecting into the water to be treated a flocculant of a dosing amount corresponding to the treatment state, wherein the monitoring means is a flocculation monitoring apparatus monitoring the treatment state of the water to be treated that is subjected to a flocculation treatment, and includes a measurement-light applying part applying a measurement light to a measurement region of the water to be treated, a scattered-light receiving part receiving a scattered light due to particles of the water to be treated in the measurement region, a signal processing part that converts a light reception output from the scattered-light receiving part into an output signal indicating a level corresponding to the intensity of the scattered light; and a measurement value arithmetic part including an amplitude measuring means measuring a peak-to-peak amplitude of the output signal, the measurement value arithmetic part calculating an occurrence rate or occurrence frequency of a specific peak-to-peak amplitude by monitoring an appearance of the peak-to-peak amplitude and aggregating appearing peak-to-peak amplitudes, the measurement value arithmetic part calculating an index related to flocculation of the water to be treated, the index related to the flocculation indicating a particle diameter of flocs in the water to be treated, wherein the amplitude measuring means detects first inflection points at which the output signal changes from rising to falling and second inflection points at which the output signal changes from falling to rising, and measures a level difference between one of the first inflection points and one of the second inflection points that are adjacent to each other, as the peak-to-peak amplitude, and wherein the dosing means adjusts an injection amount of the flocculant based on the index related to the flocculation.

* * * * *